United States Patent
Kho et al.

(10) Patent No.: US 9,299,936 B2
(45) Date of Patent: Mar. 29, 2016

(54) ORGANIC LIGHT-EMITTING DIODE INCLUDING MULTI-LAYERED HOLE TRANSPORTING LAYER, AND FLAT DISPLAY DEVICE INCLUDING THE ORGANIC LIGHT-EMITTING DIODE

(75) Inventors: Sam-Il Kho, Yongin (KR); Mie-Hwa Park, Yongin (KR); Hye-In Jeong, Yongin (KR); Yoon-Hyun Kwak, Yongin (KR); Dae-Yup Shin, Yongin (KR); Kwan-Hee Lee, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 731 days.

(21) Appl. No.: 13/543,714

(22) Filed: Jul. 6, 2012

(65) Prior Publication Data

US 2013/0140530 A1 Jun. 6, 2013

(30) Foreign Application Priority Data

Dec. 2, 2011 (KR) .................. 10-2011-0128526

(51) Int. Cl.
*H01L 51/54* (2006.01)
*H01L 51/00* (2006.01)
*H01L 51/50* (2006.01)

(52) U.S. Cl.
CPC .......... *H01L 51/0067* (2013.01); *H01L 51/006* (2013.01); *H01L 51/0061* (2013.01); *H01L 51/5064* (2013.01)

(58) Field of Classification Search
CPC ... H01L 27/32; H01L 51/006; H01L 51/0061; H01L 51/0067; H01L 51/50; H01L 51/5064; H05B 33/14; C09K 11/00
See application file for complete search history.

(56) References Cited

U.S. PATENT DOCUMENTS

| 6,565,996 | B2 | 5/2003 | Hatwar et al. | |
|---|---|---|---|---|
| 9,006,721 | B2 | 4/2015 | Lee et al. | |
| 2003/0048072 | A1* | 3/2003 | Ishihara et al. | 313/506 |
| 2005/0106419 | A1 | 5/2005 | Endoh et al. | |
| 2005/0121667 | A1 | 6/2005 | Kuehl et al. | |
| 2005/0221124 | A1 | 10/2005 | Hwang et al. | |
| 2006/0188745 | A1* | 8/2006 | Liao et al. | 428/690 |
| 2006/0240277 | A1* | 10/2006 | Hatwar et al. | 428/690 |
| 2007/0141396 | A1 | 6/2007 | Chun et al. | |
| 2008/0014464 | A1* | 1/2008 | Kawamura et al. | 428/690 |
| 2009/0167161 | A1 | 7/2009 | Yabunouchi et al. | |
| 2009/0218933 | A1* | 9/2009 | Matsushima et al. | 313/504 |
| 2010/0109000 | A1 | 5/2010 | Mathai et al. | |
| 2010/0219404 | A1* | 9/2010 | Endo et al. | 257/40 |
| 2011/0084258 | A1 | 4/2011 | Kim et al. | |
| 2011/0193074 | A1 | 8/2011 | Lee et al. | |
| 2011/0215308 | A1 | 9/2011 | Im et al. | |
| 2011/0233525 | A1 | 9/2011 | Terao et al. | |
| 2011/0248251 | A1* | 10/2011 | Yamamoto et al. | 257/40 |
| 2013/0032788 | A1* | 2/2013 | Lee et al. | 257/40 |
| 2013/0140530 | A1* | 6/2013 | Kho et al. | 257/40 |
| 2013/0153865 | A1* | 6/2013 | Kho et al. | 257/40 |
| 2014/0246663 | A1* | 9/2014 | Kambe et al. | 257/40 |

FOREIGN PATENT DOCUMENTS

| CN | 1458141 A | 11/2003 |
|---|---|---|
| CN | 102201432 A | 9/2011 |
| JP | 2005-166641 A | 6/2005 |
| KR | 10-2005-0054427 | 6/2005 |
| KR | 10-2005-0097670 | 10/2005 |
| KR | 10-2007-0068147 | 6/2007 |
| KR | 10-2009-0098930 | 9/2009 |
| KR | 10-2010-0039815 | 4/2010 |
| KR | 10-2010-0043994 | 4/2010 |
| KR | 10-2010-0068617 | 6/2010 |
| KR | 10-2010-0094819 | 8/2010 |
| KR | 10-2010-0095504 | 8/2010 |
| KR | 10-2010-0097180 | 9/2010 |
| KR | 10-2011-0039812 | 4/2011 |
| KR | 10-2011-0089142 | 8/2011 |
| WO | WO 2009/069434 | 6/2009 |

OTHER PUBLICATIONS

U.S. Notice of Allowance dated Jul. 15, 2015, for cross reference U.S. Appl. No. 13/467,960, (8 pages).

* cited by examiner

*Primary Examiner* — Dawn L. Garrett
(74) *Attorney, Agent, or Firm* — Christie, Parker & Hale, LLP

(57) ABSTRACT

An organic light-emitting diode including: a first mixed layer between an emission layer and a first electrode and including first and second compounds; a second mixed layer between the emission layer and the first mixed layer and including third and fourth compounds; a first charge generation layer between the first mixed layer and the first electrode and including the first and second compounds and a first charge generation material; a second charge generation layer between the first mixed layer and the second mixed layer and including the third and fourth compounds and a second charge generation material; and a buffer layer between the emission layer and the second mixed layer, the first and the third compounds are each independently a compound represented by Formula 1 below, and the second compound and fourth compounds are each independently a compound represented by Formula 2 below:

Formula 1

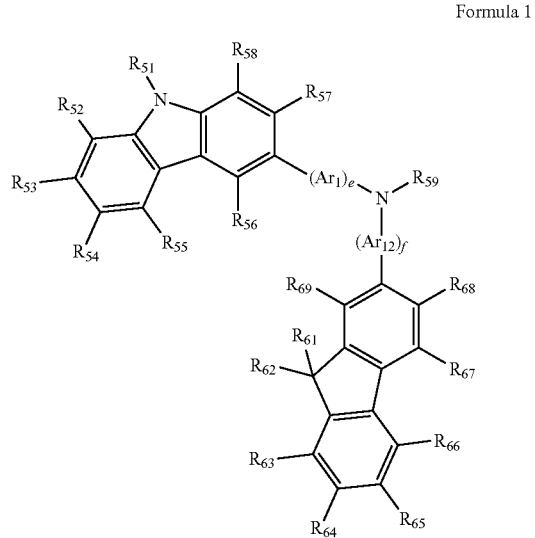

-continued

Formula 2

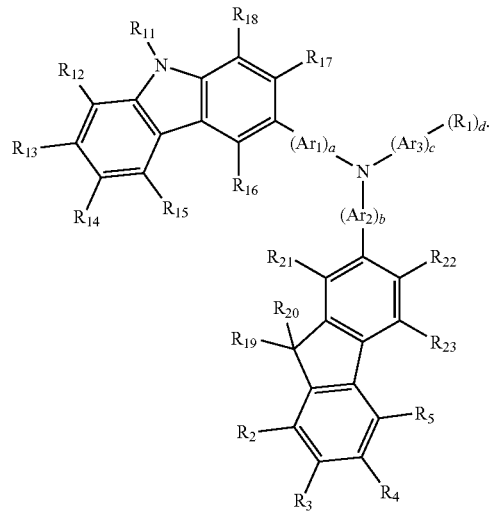

20 Claims, 4 Drawing Sheets

ORGANIC LIGHT-EMITTING DIODE INCLUDING MULTI-LAYERED HOLE TRANSPORTING LAYER, AND FLAT DISPLAY DEVICE INCLUDING THE ORGANIC LIGHT-EMITTING DIODE

CROSS-REFERENCE TO RELATED PATENT APPLICATION

This application claims priority to and the benefit of Korean Patent Application No. 10-2011-0128526, filed on Dec. 2, 2011, in the Korean Intellectual Property Office, the disclosure of which is incorporated herein in its entirety by reference.

BACKGROUND

1. Field

The following description relates to an organic light-emitting diode including a multi-layered hole transporting layer and a flat display device including the organic light-emitting diode.

2. Description of Related Art

Organic light emitting diodes are self-emission devices and enable generation of multi-color images. In addition, the organic light emitting diodes have a wide viewing angle, a high contrast ratio, a short response time, and excellent brightness, driving voltage, and response speed characteristics.

In a typical organic light-emitting diode, an anode is formed on a substrate, and a hole transport layer, an emission layer, an electron transport layer, and a cathode are sequentially formed in this stated order on the anode. In this regard, the hole transport layer, the emission layer, and the electron transport layer are organic films including organic compounds. When a voltage is applied between the anode and the cathode, holes injected from the anode pass through the hole transport layer and migrate toward the emission layer, and electrons injected from the cathode pass through the electron transport layer and migrate toward the emission layer. The holes and electrons, which are carriers, are recombined in the emission layer to generate excitons, and then the excitons change from an excited state to a ground state, thereby generating light.

A hole transport material used in a hole transporting layer has, in general, excellent hole injection function or hole transport function, thereby forming a device with a low driving voltage. That is, if a hole transport material having high hole mobility is used in a hole transporting layer, the driving voltage of the formed device is substantially decreased. However, charges are excessively injected and thus, a formed device may have low efficiency and a short lifespan (lifetime). To resolve these problems, many efforts have been made.

SUMMARY

An aspect of an embodiment of the present invention is directed toward an organic light-emitting diode including a multi-layered hole transporting layer that includes two different hole transporting compounds to improve the efficiency and lifespan (lifetime) of a formed device.

An aspect of an embodiment of the present invention is directed toward a flat display device including the organic light-emitting diode.

Aspects of embodiments of the present invention are directed toward an organic light-emitting diode including: a hole transporting layer that includes a plurality of layers including combinations of materials having different hole injection characteristics, electrical stability characteristics and/or charge generation characteristics; and a flat display device including the organic light-emitting diode. Here, the organic light-emitting diode has high stability due to improved charge balance.

According to an embodiment of the present invention, there is provided an organic light-emitting diode that includes: a first electrode; a second electrode facing the first electrode; an emission layer interposed between the first electrode and the second electrode; a first mixed layer that is disposed between the emission layer and the first electrode and includes a first compound and a second compound; a second mixed layer that is disposed between the emission layer and the first mixed layer and includes a third compound and a fourth compound; a first charge generation layer that is disposed between the first mixed layer and the first electrode and includes the first compound, the second compound, and a first charge generation material; a second charge generation layer that is disposed between the first mixed layer and the second mixed layer and includes the third compound, the fourth compound, and a second charge generation material; and a buffer layer that is disposed between the emission layer and the second mixed layer, wherein the first compound and the third compound are each independently a compound represented by Formula 1 below, and the second compound and the fourth compound are each independently a compound represented by Formula 2 below:

Formula 1

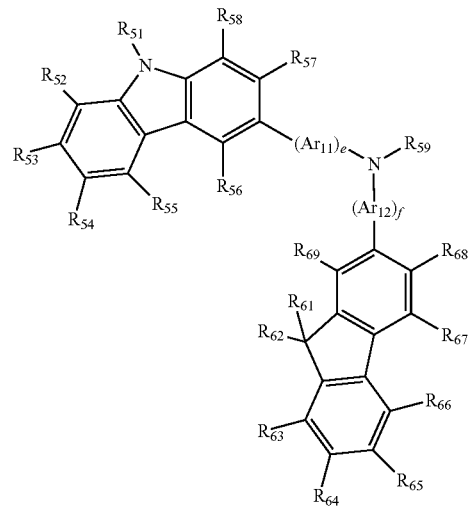

wherein in Formula 1, $Ar_{11}$ and $Ar_{12}$ are each independently a substituted or unsubstituted $C_5$-$C_{60}$ arylene group; e and f are each independently an integer of 0 to 5; $R_{51}$ to $R_{58}$ and $R_{61}$ to $R_{69}$ are each independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group; and $R_{59}$ is a phenyl group, a naphthyl group, an anthryl group, a biphenyl group, or a pyridyl group or is a phenyl group, a naphthyl group, an anthryl group, a biphenyl group, or a pyridyl group of which at least one hydrogen atom is substituted with at least one of a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{20}$ alkyl group, and a substituted or unsubstituted $C_1$-$C_{20}$ alkoxy; and Formula 2

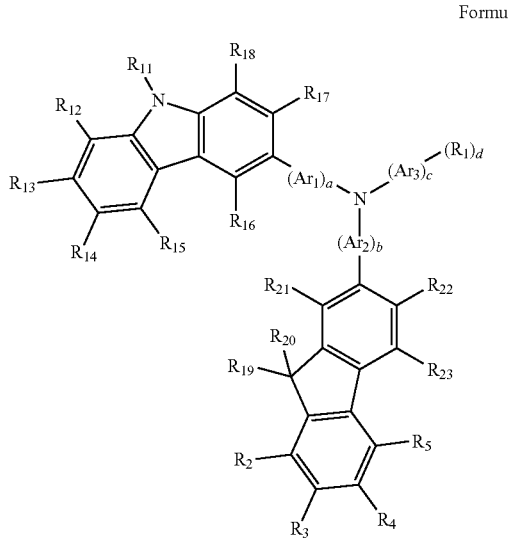

wherein in Formula 2, $Ar_1$ to $Ar_3$ are each independently a substituted or unsubstituted $C_5$-$C_{60}$ arylene group; a and b are each independently an integer of 0 to 5; c is an integer of 1 to 5; $R_1$ to $R_5$ are each independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, —Si($R_{31}$)($R_{32}$)($R_{33}$), —N($R_{34}$)($R_{35}$), or a nitrogen atom-containing group, and at least one of $R_1$ to $R_5$ is a nitrogen atom-containing group; d is an integer of 0 to 5; $R_{11}$ to $R_{23}$ are each independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, —Si($R_{36}$)($R_{37}$)($R_{38}$), or —N($R_{39}$)($R_{40}$); and $R_{31}$ to $R_{40}$ are each independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, or a substituted or unsubstituted $C_2$-$C_{60}$ heteroaryl group, wherein the nitrogen atom-containing group is a 5-membered aromatic ring group that includes a nitrogen atom as a ring atom, a 6-membered aromatic ring group that includes a nitrogen atom as a ring atom, or a 9-membered aromatic ring group that includes a nitrogen atom as a ring atom and is formed by fusing a 5-membered aromatic group and a 6-membered aromatic group.

A highest occupied molecular orbital (HOMO) energy level of the second compound may be 0.1 eV to 0.2 eV lower than a HOMO energy level of the first compound, and a lowest unoccupied molecular orbital (LUMO) energy level of the second compound may be 0.1 eV to 0.2 eV lower than a LUMO energy level of the first compound.

A hole mobility of the first compound may be higher than a hole mobility of the second compound.

A mixed weight ratio of the first compound to the second compound may be in a range of 6:4 to 8:2.

A mixed weight ratio of the third compound to the fourth compound may be in a range of 6:4 to 8:2.

Thicknesses of the first mixed layer and the second mixed layer may each be independently in a range of 40 nm to 60 nm.

An amount of the first charge generation material may be in a range of 1 to 3 parts by weight based on 100 parts by weight of the first charge generation layer.

An amount of the second charge generation material may be in a range of 1 to 3 parts by weight based on 100 parts by weight of the second charge generation layer.

Thicknesses of the first charge generation layer and the second charge generation layer may each be independently in a range of 10 nm to 20 nm.

The buffer layer may include the compound represented by Formula 1.

A thickness of the buffer layer may be in a range of 0.1 nm to 30 nm.

The first mixed layer and the first charge generation layer may contact each other.

The second mixed layer and the second charge generation layer may contact each other.

The organic light-emitting diode may include at least one layer of a hole blocking layer, an electron transporting layer, an electron injection layer, and a functional layer having an electron transport function and an electron injection function, wherein the at least one layer is interposed between the emission layer and the second electrode.

According to another embodiment of the present invention, there is provided a flat display device including: a transistor including a source, a drain, a gate, and an active layer; and the above described organic light-emitting diode, wherein the first electrode of the organic light-emitting diode is electrically connected to the source or the drain.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION

Figure 1:
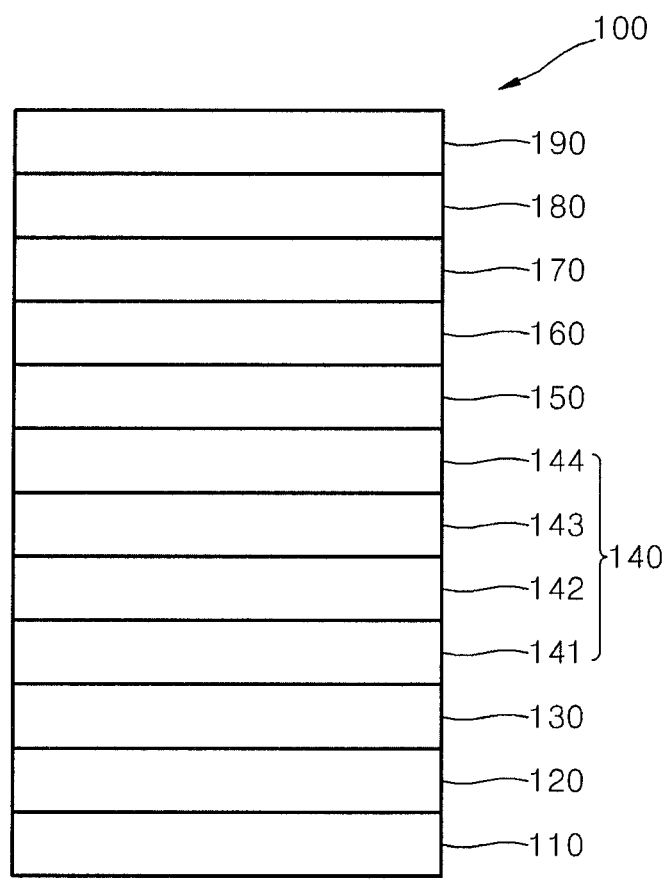
FIG. 1 is a schematic view of an organic light-emitting diode according to an embodiment of the present invention.

Expressions such as "at least one of," when preceding a list of elements, modify the entire list of elements and do not modify the individual elements of the list.

According to an embodiment of the present invention, there is provided an organic light-emitting diode that includes a first electrode; a second electrode facing the first electrode; an emission layer interposed between the first electrode and the second electrode; a first mixed layer that is disposed between the emission layer and the first electrode and includes a first compound and a second compound; a second mixed layer that is disposed between the emission layer and the first mixed layer and includes a third compound and a fourth compound; a first charge generation layer that is disposed between the first mixed layer and the first electrode and includes the first compound, the second compound, and a first charge generation material; a second charge generation layer that is disposed between the first mixed layer and the second mixed layer and includes the third compound, the fourth compound, and a second charge generation material; and a buffer layer that is disposed between the emission layer and the second mixed layer, wherein the first compound and the third compound may each be independently a compound represented by Formula 1 below, and the second compound and the fourth compound may each be independently a compound represented by Formula 2 below.

That is, in one embodiment, the first compound and the third compound are each independently a compound represented by Formula 1:

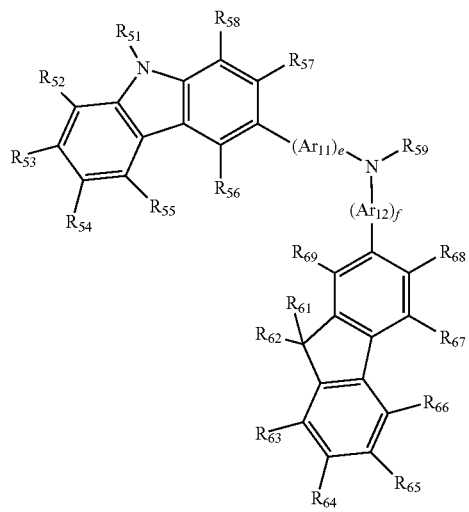

Formula 1 wherein in Formula 1, $Ar_{11}$ and $Ar_{12}$ may each be independently a substituted or unsubstituted $C_5$-$C_{60}$ arylene group.

For example, $Ar_{11}$ and $Ar_{12}$ may each be independently a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, or a substituted or unsubstituted hexacenylene.

In Formula 1, e and f may each be independently an integer of 0 to 5.

If e and/or f is 0, a carbazol ring and/or fluorine ring of Formula 1 may be directly linked to a nitrogen atom located at the center of the chemical structure represented by Formula 1. For example, e and f may each be 0, 1, or 2, but are not limited thereto. If e is two or more, two (2) or more $Ar_{11}$ may be identical to or different from each other. Also, if f is two or more, two or more $Ar_{12}$ may be identical to or different from each other.

In Formula 1, $R_{51}$ to $R_{58}$ and $R_{61}$ to $R_{69}$ may each be independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group.

In Formula 1, $R_{59}$ may be at least one of a phenyl group; a naphthyl group; an anthryl group; a biphenyl group; a pyridyl group; or a phenyl group, a naphthyl group, an anthryl group, a biphenyl group, or a pyridyl group of which at least one hydrogen atom is substituted with at least one of a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{20}$ alkyl group, and a substituted or unsubstituted $C_1$-$C_{20}$ alkoxy.

According to an embodiment of the present invention, the first compound and the third compound may each be independently represented by Formula 1A below:

Formula 1A

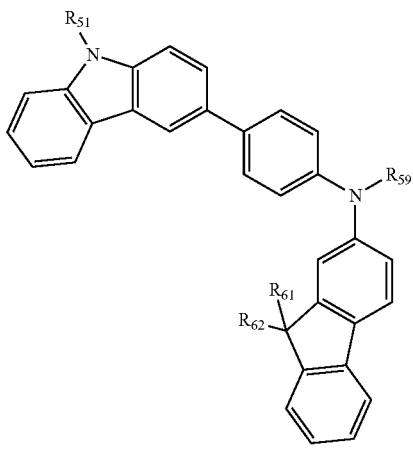

wherein in Formula 1A, $R_{51}$, $R_{59}$, $R_{61}$, and $R_{62}$ are the same as described with reference to Formula 1.

For example, the first compound and the third compound may each be Compound 301 below, but are not limited thereto:

Compound 301

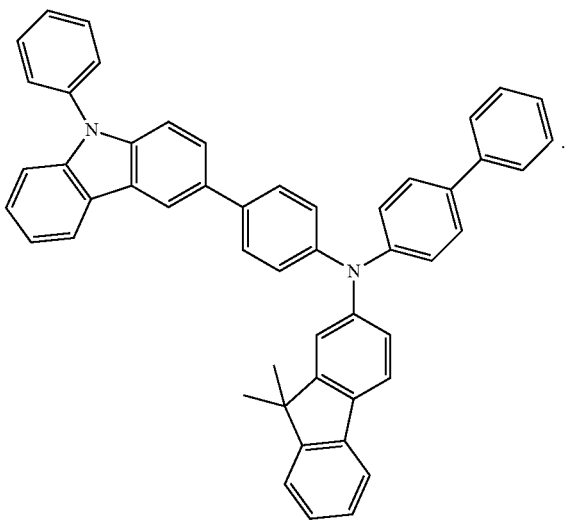

In one embodiment, the second compound and the fourth compound are each independently a compound represented by Formula 2:

Formula 2

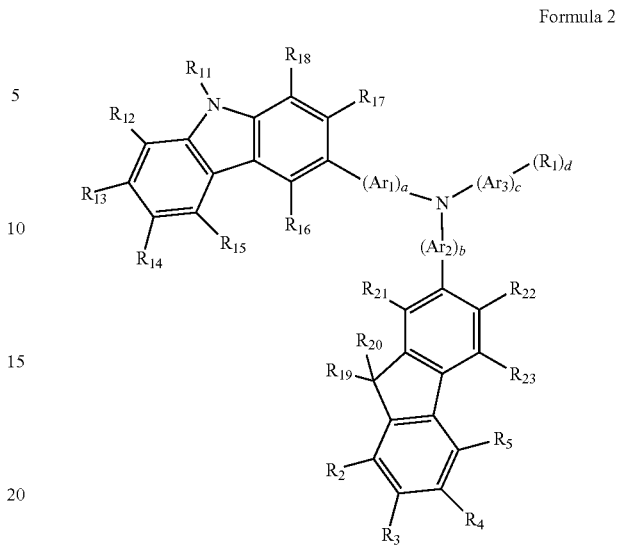

wherein in Formula 2, $Ar_1$ to $Ar_3$ may each be independently a substituted or unsubstituted $C_5$-$C_{60}$ arylene group.

For example, $Ar_1$ to $Ar_3$ may each be independently a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentacenylene group, or a substituted or unsubstituted hexacenylene group.

In Formula 2, a and b may each be independently an integer of 0 to 5. If a and/or b is 0, a carbazol ring and/or fluorine ring of Formula 1 may be directly linked to a nitrogen atom located at the center of the chemical structure represented by Formula 1. For example, a and b may each be 0, 1, or 2, but are not limited thereto. If a is two or more, two or more $Ar_1$ may be identical to or different from each other. Also, if b is two or more, two or more $Ar_2$ may be identical to or different from each other.

In Formula 2, c is an integer of 1 to 5. Because c is an integer of 1 to 5, $Ar_3$ is necessarily present in Formula 1. For example, c may be 1 or 2, but is not limited thereto. If c is two or more, two or more $Ar_3$ may be identical to or different from each other.

In Formula 2, $R_1$ to $R_5$ may each be independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, —Si($R_{31}$)($R_{32}$)($R_{33}$), —N($R_{34}$)($R_{35}$), or a nitrogen atom-containing group, wherein at least one of $R_1$ to $R_5$ is a nitrogen atom-containing group ($R_{31}$ to $R_{35}$ are presented below).

For example, $R_1$ to $R_5$ may each be independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{10}$ alkyl group, a substituted or unsubstituted $C_1$-$C_{10}$ alkoxy group, a substituted or unsubstituted $C_5$-$C_{20}$ aryl group, or a nitrogen atom-containing group, and at least one of $R_1$ to $R_5$ may be a nitrogen atom-containing group.

Herein, the nitrogen atom-containing group is a 5-membered aromatic ring group that includes a nitrogen atom as a ring atom, a 6-membered aromatic ring group that includes a nitrogen atom as a ring atom, or a 9-membered aromatic ring group that includes a nitrogen atom as a ring atom and is formed by fusing a 5-membered aromatic group and a 6-membered aromatic group. For example, the nitrogen atom-containing group may be represented by one of Formulae 4A to 4P below:

Formula 4A
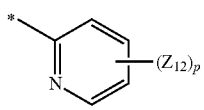

Formula 4B
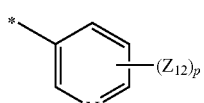

Formula 4C
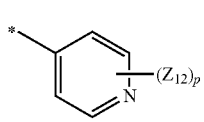

Formula 4D
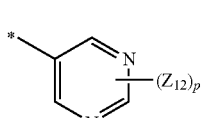

Formula 4E
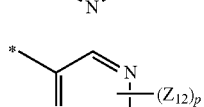

Formula 4F
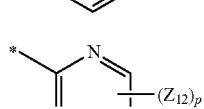

Formula 4G
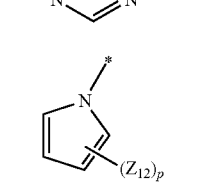

-continued

Formula 4H
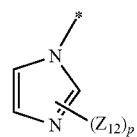

Formula 4I
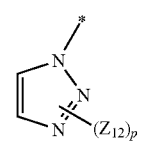

Formula 4J
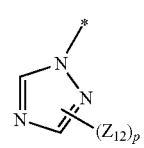

Formula 4K
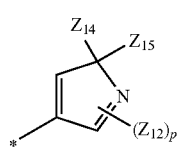

Formula 4L
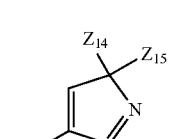

Formula 4M
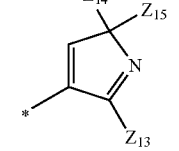

Formula 4N
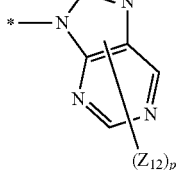

Formula 4O
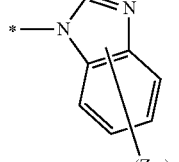

Formula 4P
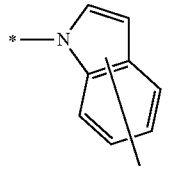

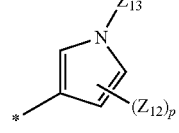

In Formulae 4A to 4P, $Z_{12}$, $Z_{13}$, $Z_{14}$, and $Z_{15}$ may each be a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a methyl group, an ethyl group, a propyl group, or a butyl group. For example, in Formulae 4A to 4P, $Z_{12}$, $Z_{13}$, $Z_{14}$ and $Z_{15}$ may all be hydrogen atoms. In Formulae 4A to 4P, p is an integer of 1 to 6. Here, p may be appropriately determined according to the structures of Formulae 4A to 4P within this range. If p is two or more, two or more $Z_{12}$ may be identical to or different from each other.

In Formula 2, d may be an integer of 0 to 5. For example, d may be 0, 1, or 2, but is not limited thereto. D may be appropriately (suitably) determined according to the structure of $Ar_3$ within this range. If d is two or more, two or more $R_1$ may be identical to or different from each other.

In Formula 2, $R_{11}$ to $R_{23}$ may each be independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, —Si($R_{36}$)($R_{37}$)($R_{38}$), or —N($R_{39}$)($R_{40}$).

For example, $R_{12}$ to $R_{18}$ and $R_{21}$ to $R_{23}$ may each be independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, or a phosphoric acid group or salt thereof, and $R_{11}$, $R_{19}$, and $R_{20}$ may each be independently a hydrogen atom, a methyl group, an ethyl group, a propyl group, a butyl group, a pentyl group, a phenyl group, a naphthyl group, an anthryl group, a fluorenyl group, or a pyrenyl group, but are not limited thereto.

In regard to —Si($R_{31}$)($R_{32}$)($R_{33}$), —N($R_{34}$)($R_{35}$), —Si($R_{36}$)($R_{37}$)($R_{38}$) and —N($R_{39}$)($R_{40}$), $R_{31}$ to $R_{40}$ may each be independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, or a substituted or unsubstituted $C_2$-$C_{60}$ heteroaryl. For example, $R_{31}$ to $R_{40}$ may each be independently a hydrogen atom; a deuterium atom; a halogen atom; a hydroxyl group; a cyano group; a nitro group; an amino group; an aminidino group; hydrazine; hydrazone; a carboxylic group or salt thereof; a sulfonic acid group or salt thereof; a phosphoric acid group or salt thereof; a $C_1$-$C_{10}$ alkyl group (for example, a methyl group, an ethyl group, a propyl group, a butyl group, a pentyl group, or a hexyl group); a $C_1$-$C_{10}$ alkoxy group (for example, a methoxy group, an ethoxy group, a propoxy group, a butoxy group, or a pentoxy group); a $C_1$-$C_{10}$ alkyl group; a $C_1$-$C_{10}$ alkoxy group of which at least one hydrogen atom is substituted with at least one of a deuterium atom, a halogen atom, a hydroxyl group, a cyano group, a nitro group, an amino group, an amidino group, hydrazine, hydrazone, a carboxylic group or salt thereof, a sulfonic acid group or salt thereof, and a phosphoric acid group or salt thereof; a phenyl group; a naphthyl group; an anthryl group; a fluorenyl group; a pyrenyl group; or a phenyl group, a naphthyl group, an anthryl group, a fluorenyl group, or a pyrenyl group of which at least one hydrogen atom is substituted with at least one of a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a $C_1$-$C_{10}$ alkyl group, and a $C_1$-$C_{10}$ alkoxy group, but are not limited thereto.

In Formula 2, $R_1$ may be a nitrogen atom-containing group, and c and d may each be independently 1 or 2. In some embodiments, in Formula 2, at least one of $R_2$ to $R_5$ may be a nitrogen atom-containing group.

According to an embodiment of the present invention, the second compound and the fourth compound may each be independently a compound represented by one of Formulae 2A to 2K:

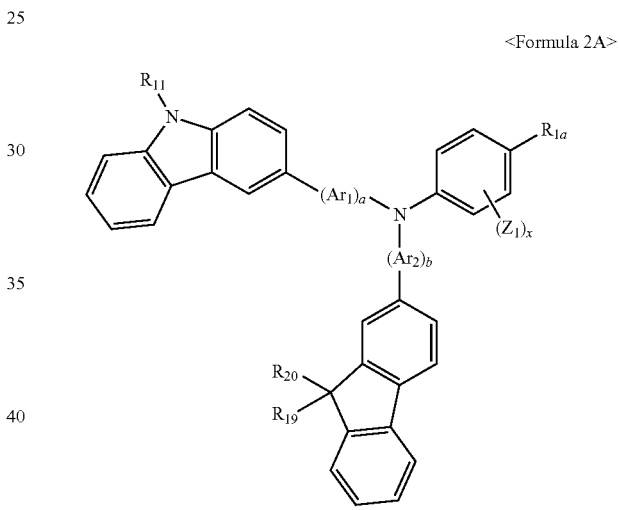

<Formula 2A>

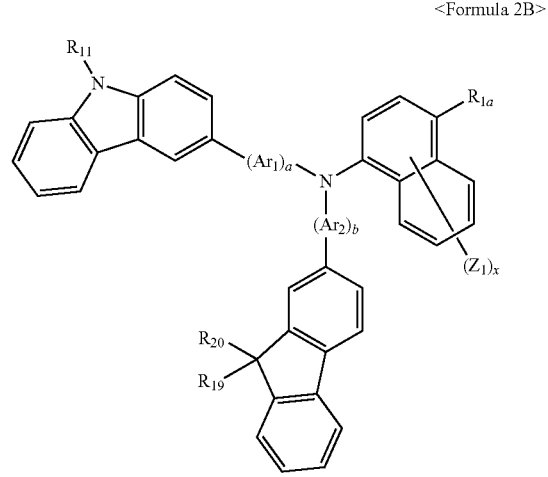

<Formula 2B>

<Formula 2C>
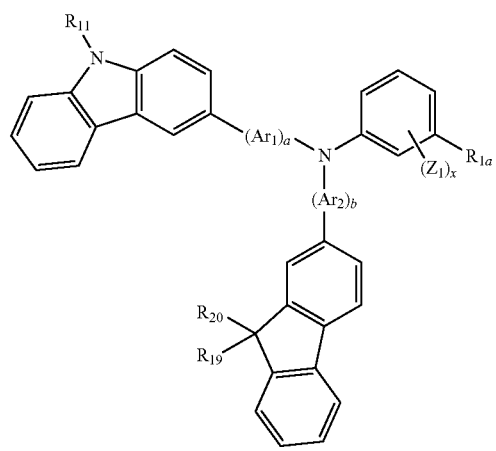
<Formula 2D>
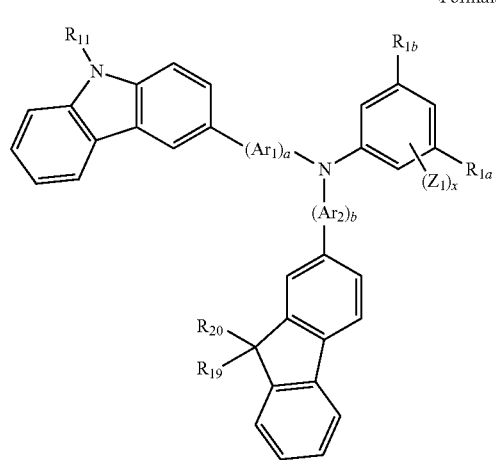
<Formula 2E>
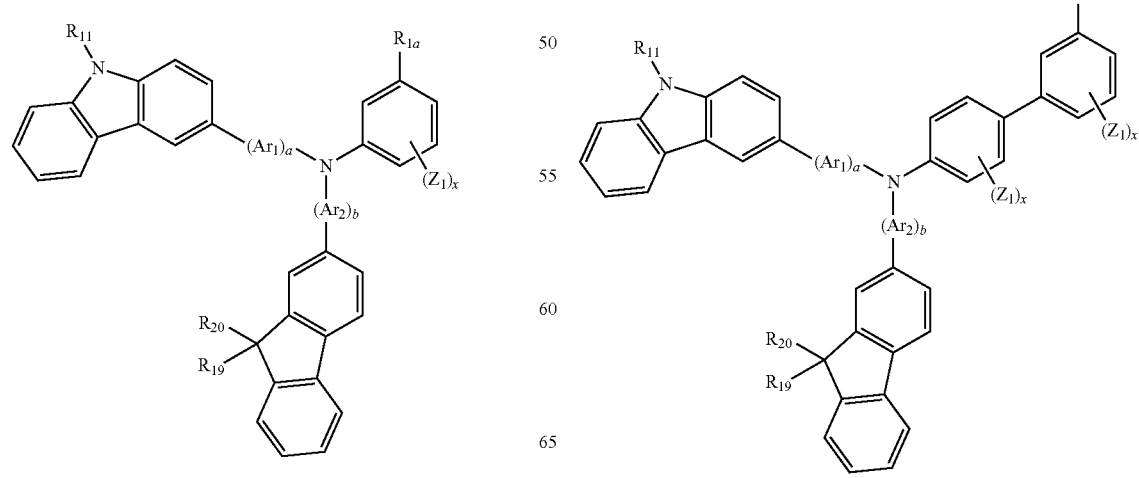
<Formula 2F>
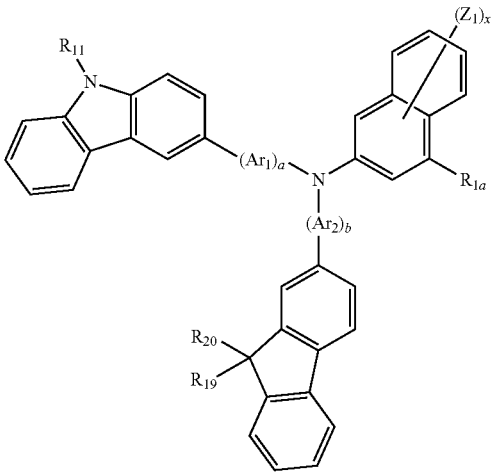
<Formula 2G>
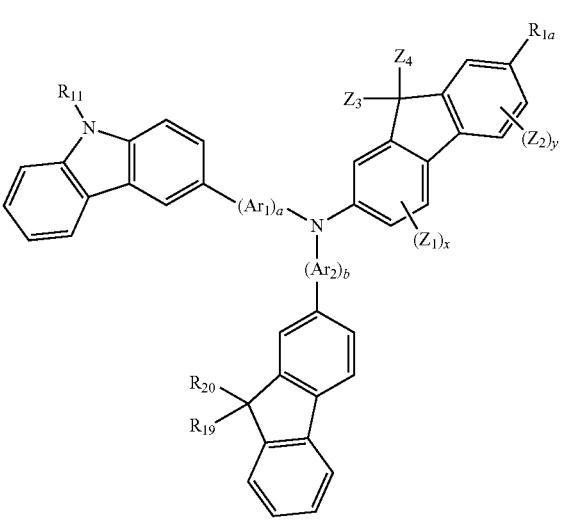
<Formula 2H>

-continued

<Formula 2I>

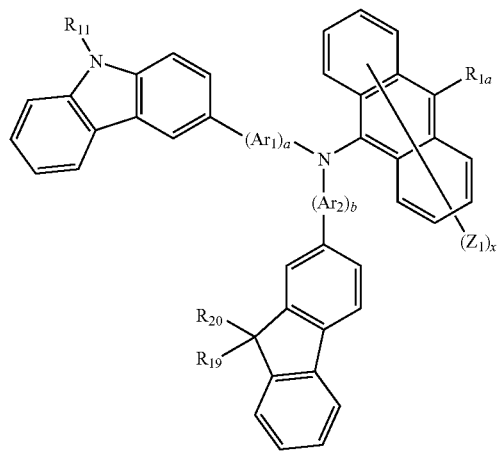

<Formula 2J>

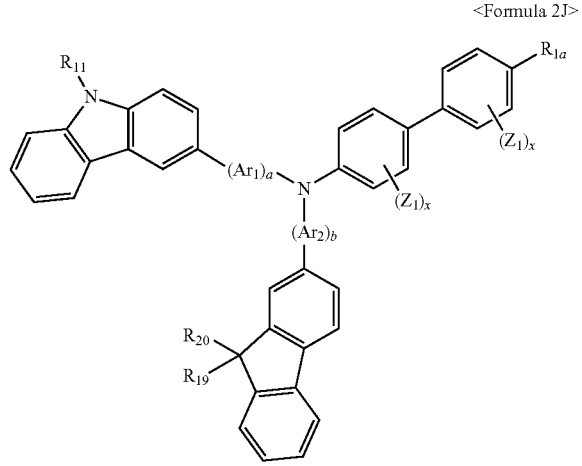

<Formula 2K>

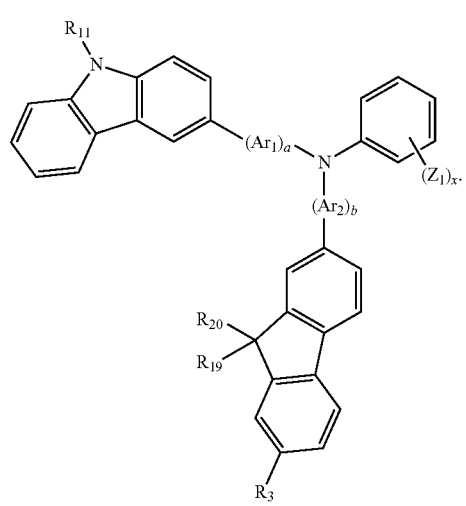

In Formulae 2A to 2K, $Ar_1$, $Ar_2$, a, and b are the same as described with reference to Formula 2, and $R_{1a}$, $R_{1b}$, and $R_3$ may each be independently a nitrogen atom-containing group. The nitrogen atom-containing group has been already described above.

In Formulae 2A to 2K, $R_{11}$, $R_{19}$ and $R_{20}$ may each be independently a substituted or unsubstituted $C_1$-$C_{60}$ alkyl group, or a substituted or unsubstituted $C_5$-$C_{60}$ aryl group.

In Formulae 2A to 2K, $Z_1$ to $Z_4$ may each be independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, —Si($Q_1$)($Q_2$)($Q_3$), or —N($Q_4$)($Q_5$), and if x or y is 2 or more, a plurality of $Z_1$ or $Z_2$ may be identical to or different from each other. Also, x may be an integer of 1 to 8, and y may be an integer of 1 to 3.

Herein, $Q_1$ to $Q_5$ may each be independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, a substituted or unsubstituted $C_5$-$C_{60}$ arylthio group, or a substituted or unsubstituted $C_2$-$C_{60}$ heteroaryl group.

For example, the second compound and the fourth compound may each be independently one of Compounds 2, 8, 14, 15, 16, 20, 31, and 35, but are not limited thereto:

COMPOUND 2

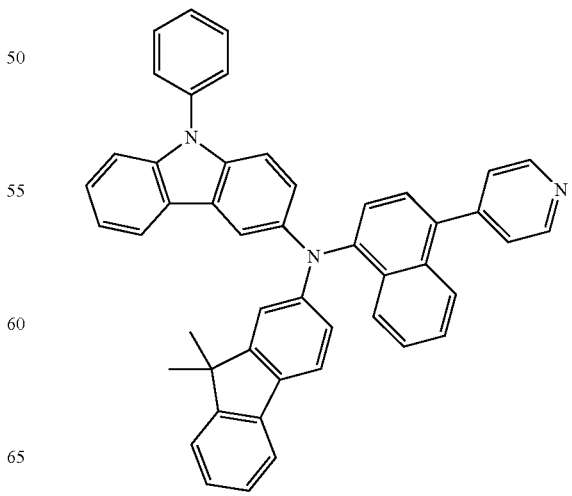

COMPOUND 8
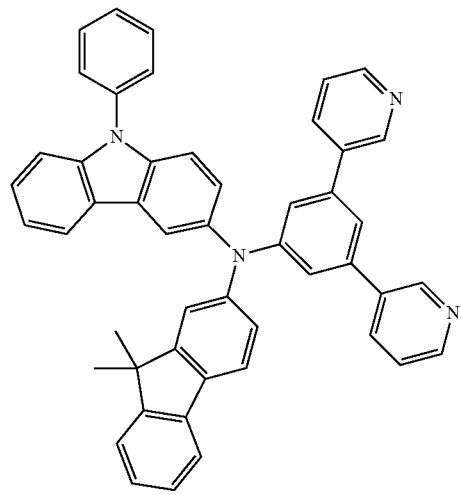
COMPOUND 15
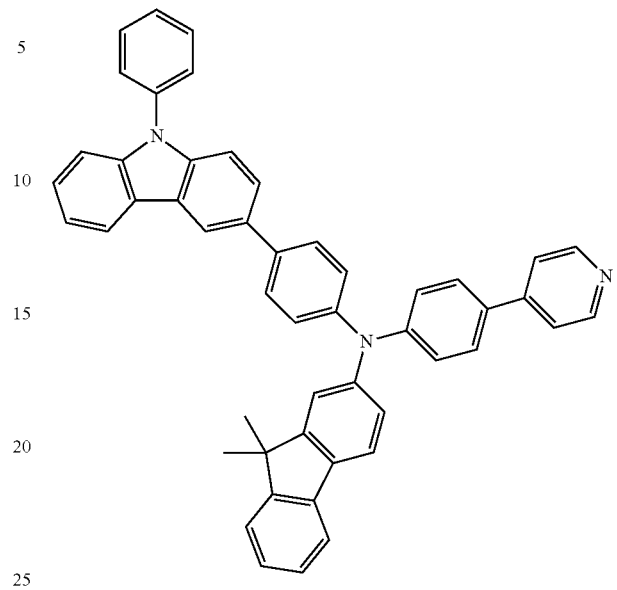
COMPOUND 14
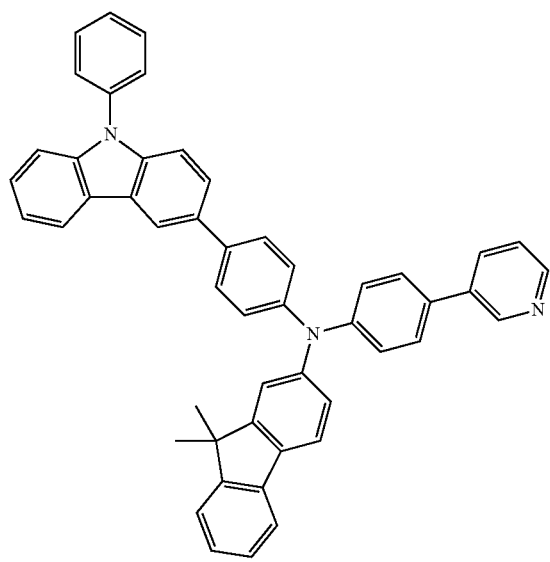
COMPOUND 16
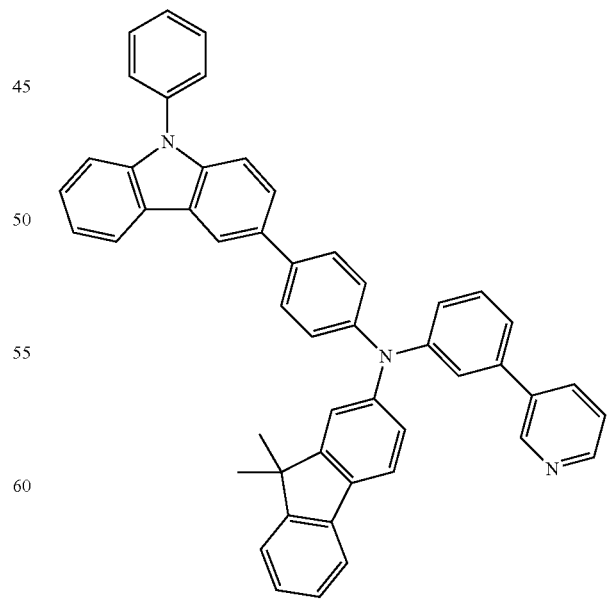

COMPOUND 20

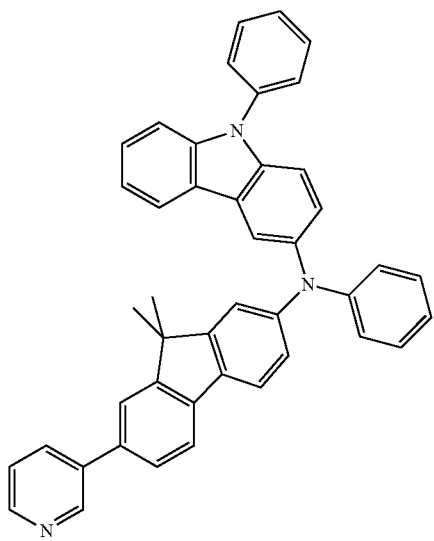

COMPOUND 35

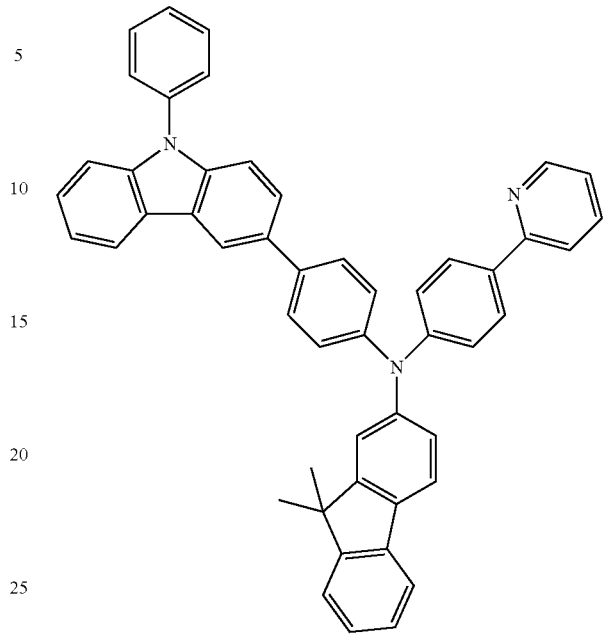

COMPOUND 31

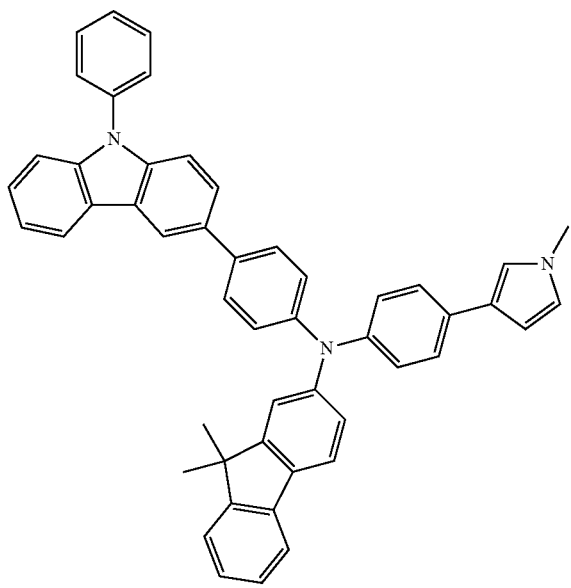

The first compound has high hole mobility and facilitates hole transport due to its high hole mobility. The second compound is a material that has better electron trapping function than the first compound.

If the first compound is mixed with the second compound that has a lower lowest unoccupied molecular orbital (LUMO) energy level than the first compound by 0.1 eV to 0.2 eV, the electron trapping function of the first compound may be enhanced. Thus, quenching of excitons may be reduced and a formed device may have prolonged lifespan (lifetime).

For example, a highest occupied molecular orbital (HOMO) energy level of the second compound may be 0.1 eV to 0.2 eV lower than a HOMO energy level of the first compound, and the LUMO energy level of the second compound may be 0.1 eV to 0.2 eV lower than a LUMO energy level of the first compound. If the HOMO and LUMO energy level differences between the first and second compounds are within these ranges, electrons may be trapped without a substantial increase in driving voltage and thus, injected charges may easily migrate and energy transition may easily occur, and a formed device may have improved lifespan (lifetime) characteristics.

An amount of the second compound may be in a range of 20 to 40 wt % based on the total amount of the first and second compounds. If the amount of the second compound is within this range, the electron trapping characteristics and driving voltage increase prevention characteristics caused by the addition of the second compound may reach satisfactory levels.

A hole mobility of the first compound may be higher than a hole mobility of the second compound. That is, the second compound traps electrons to reduce quenching of excitons, and the first compound contributes to high hole mobility.

The first charge generation material and the second charge generation material may each be, for example, a compound having at least one cyano group. The first charge generation material and the second charge generation material may each function as a charge generation material. Non-limiting examples of the first charge generation material and the second charge generation material are quinon derivaties, such as tetracyanoquinonedimethane (TCNQ) and 2,3,5,6-tetrafluoro-tetracyano-1,4-benzoquinonedimethane(F4-CTNQ), but are not limited thereto.

The first charge generation material and the second charge generation material may each independently include at least one of Compounds 501 and 502 below.

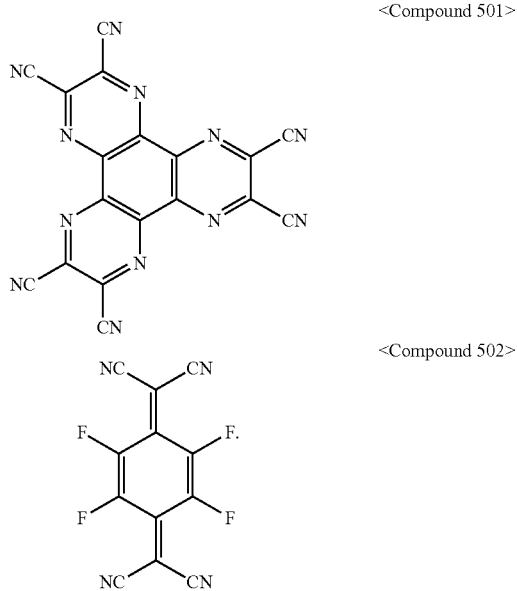

<Compound 501>

<Compound 502>

The term "substituted A" in the term "substituted or unsubstituted A (where A is an arbitrary substituent)" used herein refers to a case in which one or more hydrogen atoms of the A are substituted with a deuterium atom, a halogen atom, a hydroxyl group, a cyano group, a nitro group, a carboxyl group, a silyl group, or a salt derivative thereof, a sulfonic acid group or a salt derivative thereof, a phosphoric acid group or a salt derivative thereof, a $C_1$-$C_{50}$ alkyl group, a $C_2$-$C_{50}$ alkenyl group, a $C_2$-$C_{50}$ alkynyl group, a $C_1$-$C_{50}$ alkoxy group, a $C_3$-$C_{50}$ cycloalkyl group, a $C_3$-$C_{50}$ cycloalkenyl group, a $C_5$-$C_{60}$ aryl group, a $C_5$-$C_{60}$ aryloxy group, a $C_5$-$C_{60}$ arylthio group, a $C_2$-$C_{60}$ heteroaryl group, a $C_2$-$C_{60}$ fused polycyclic group, a group represented by $N(Q_{101})(Q_{102})$, or a group represented by $Si(Q_{103})(Q_{104})(Q_{105})$, wherein $Q_{101}$ to $Q_{105}$ may each be independently a hydrogen atom, a deuterium atom, a halogen atom, a hydroxyl group, a cyano group, an amino group, a nitro group, a nitrile group, a carboxyl group, a silyl group, a $C_1$-$C_{50}$ alkyl group, a $C_2$-$C_{50}$ alkenyl group, a $C_2$-$C_{50}$ alkynyl group, a $C_1$-$C_{50}$ alkoxy group, a $C_3$-$C_{50}$ cycloalkyl group, a $C_3$-$C_{50}$ cycloalkenyl group, a $C_5$-$C_{60}$ aryl group, a $C_5$-$C_{60}$ aryloxy group, a $C_5$-$C_{60}$ arylthio group, a $C_5$-$C_{60}$ heteroaryl group, or a $C_2$-$C_{60}$ fused polycyclic.

For example, the term "substituted A" refers to a case in which one or more hydrogen atoms of the A are substituted with a deuterium atom, a halogen atom, a hydroxyl group, a cyano group, a nitro group, a nitrile group, a carboxyl group, a silyl group, a methyl group, an ethyl group, a propyl group, a butyl group, an isobutyl group, a pentyl group, a phenyl group, a non-phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthryl group, a fluorantenyl group, a triphenylenyl group, a pyrenyl group, a chricenyl group, a naphthacenyl group, a pycenyl group, a perylenyl group, a pentaphenyl group, a hexacenyl group, a pyrrolyl group, an imidazolyl group, a benzoimidazolyl group, a phenylbenzoimidazolyl group, a pyrazolyl group, a pyridinyl group, a phenylpyridinyl group, a phenylimidazopyridinyl group, a pyrazinyl group, a pyrimidinyl group, a phenylimidazopyrimidinyl group, a pyridazinyl group, an indolyl group, an isoindolyl group, an indazolyl group, a purinyl group, a quinolinyl group, a benzoquinolinyl group, a phthallazinyl group, a naphthyridinyl group, a quinoxalinyl group, a quinazolinyl group, a cynolinyl group, a carbazolyl group, a phenanthridinyl group, an acridinyl group, a phenanthrolinyl group, a phenazinyl group, a puranyl group, a benzopuranyl group, a dibenzopuranyl group, a thiophenyl group, a benzo[b]thiophenyl group, a dibenzothiophenyl group, a thiazolyl group, an isothiazolyl group, a benzothiazolyl group, an oxazolyl group, an isoxazolyl group, a benzooxazolyl group, isoxazolyla triazolyl group, a phenyltriazolyl group, a tetrazolyl group, an oxadiazolyl group, a phenyloxadiazolyl group, a triazinyl group, a phenyltriazinyl group, a group represented by $N(Q_{101})(Q_{102})$, or a group represented by $Si(Q_{103})(Q_{104})(Q_{105})$.

The unsubstituted $C_1$-$C_{50}$ alkyl group refers to a linear or branched saturated hydrocarbonyl group of alkane from which one hydrogen atom is deficient. Examples of the unsubstituted $C_1$-$C_{50}$ alkyl group are methyl, ethyl, propyl, isobutyl, sec-butyl, pentyl, iso-amyl, hexyl, etc. A substituent of the substituted $C_1$-$C_{50}$ alkyl group may be any one of the substituents presented above where the term "substituted A" is described in more detail.

The unsubstituted $C_2$-$C_{50}$ alkenyl group used herein refers to a terminal group having at least one carbon-carbon double bond at the center or at a terminal of the substituted and unsubstituted $C_2$-$C_{50}$ alkyl group. Non-limiting examples of the unsubstituted $C_2$-$C_{50}$ alkenyl group are an ethenyl group, a propenyl group, a butenyl group, a pentenyl group, a hexenyl group, a heptenyl group, an octenyl group, a propadienyl group, an isoprenyl group, and an allyl group. A substituent of the substituted $C_2$-$C_{50}$ alkenyl group may be any one of the substituents presented above where the term "substituted A" is described in more detail.

The unsubstituted $C_2$-$C_{50}$ alkynyl group used herein refers to a terminal group having at least one carbon-carbon triple bond at the center or at a terminal of the substituted and unsubstituted $C_2$-$C_{50}$ alkyl group. Non-limiting examples of the unsubstituted $C_2$-$C_{50}$ alkynyl group are acetylenyl group, etc. A substituent of the substituted $C_2$-$C_{50}$ alkynyl group may be any one of the substituents presented above where the term "substituted A" is described in more detail.

The unsubstituted $C_1$-$C_{50}$ alkoxy group used herein has a formula represented by —OY where Y is the unsubstituted $C_1$-$C_{50}$ alkyl group as defined above. Non-limiting examples of the unsubstituted $C_1$-$C_{50}$ alkoxy group are methoxy, ethoxy, isopropyloxy, butoxy, pentoxy, etc. A substituent of the substituted $C_1$-$C_{50}$ alkoxy group may be any one of the substituents presented above where the term "substituted A" is described in more detail.

The unsubstituted $C_3$-$C_{50}$ cycloalkyl group used herein refers to a cyclic saturated hydrocarbonyl group. Non-limiting examples of the unsubstituted $C_3$-$C_{50}$ cycloalkyl group are cyclopropyl group, cyclobutyl group, cyclopentyl group, cyclohexyl group, cyclooctyl group, etc. A substituent of the substituted $C_1$-$C_{50}$ cycloalkyl group may be any one of the substituents presented above where the term "substituted A" is described in more detail.

The unsubstituted $C_3$-$C_{50}$ cycloalkenyl group used herein refers to a cyclic unsaturated hydrocarbonyl group having one or more carbon double bonds that are not an aromatic ring. Non-limiting examples of the unsubstituted $C_3$-$C_{50}$ cycloalkenyl group are a cyclopropenyl group, a cyclobutenyl group, a cyclopentenyl group, a cyclohexenyl group, a cycloheptenyl group, a 1,3-cyclohexadienyl group, a 1,4-cyclohexadienyl group, a 2,4-cycloheptadienyl group, a 1,5-cyclooctadienyl group, etc. A substituent of the substituted $C_3$-$C_{50}$ cycloalkenyl group may be any one of the substituents presented above where the term "substituted A" is described in more detail.

The unsubstituted $C_5$-$C_{60}$ aryl group used herein refers to a monovalent group having a carbocyclic aromatic system in which the number of carbon atoms is 5 to 60, and may be a monocyclic group or a polycyclic group. If the unsubstituted $C_5$-$C_{60}$ aryl group is a polycyclic group, two or more rings contained in the unsubstituted $C_5$-$C_{60}$ aryl group may be fused. Non-limiting examples of the unsubstituted $C_5$-$C_{60}$ aryl group are a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphthacenyl group, a picenyl group, a perylenyl group, a pentaphenyl, and a hexacenyl. A substituent of the substituted $C_5$-$C_{60}$ aryl group may be any one of the substituents presented above where the term "substituted A" is described in more detail.

The unsubstituted $C_5$-$C_{60}$ aryloxy group used herein refers to a monovalent group wherein a carbon atom of the $C_5$-$C_{60}$ aryl group is attached via an oxygen linker (—O—). A substituent of the substituted $C_5$-$C_{60}$ aryloxy group may be any one of the substituents presented above where the term "substituted A" is described in detail.

The unsubstituted $C_5$-$C_{60}$ arylthio group used herein refers to a monovalent group wherein a carbon atom of the $C_5$-$C_{60}$ aryl group is attached via a sulfur linker (—S—). Examples of the unsubstituted $C_5$-$C_{60}$ arylthio group are a phenyl thio group, a naphthyl thio group, an indanylthio group, and an indenyl thio group. A substituent of the substituted $C_5$-$C_{60}$ arylthio group may be any one of the substituents presented above where the term "substituted A" is described in more detail.

The unsubstituted $C_2$-$C_{60}$ heteroaryl group used herein refers to a monovalent group that has at least one ring having one or more heteroatoms selected from the group consisting of nitrogen (N), oxygen (O), phosphorous (P), and sulfur (S) and that has 2 to 60 carbon atoms, and may be a monocyclic or polycyclic group. If the unsubstituted $C_2$-$C_{60}$ heteroaryl group is a polycyclic group, two or more rings contained in the unsubstituted $C_2$-$C_{60}$ heteroaryl group may be fused. Examples of the unsubstituted $C_2$-$C_{60}$ heteroaryl group are a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, anaphthyridinyl group, a quinoxalinyl group, a quinazolinyl group, a cinnolinyl group, a carbazolyl group, phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, etc. A substituent of the substituted $C_2$-$C_{60}$ heteroaryl group may be any one of the substituents presented above where the term "substituted A" is described in more detail.

The unsubstituted $C_2$-$C_{60}$ fused polycyclic group used herein refers to a monovalent group that includes two or more fused rings and 2 to 60 carbon atoms. The unsubstituted $C_2$-$C_{60}$ fused polycyclic group may be a polycyclic group, or the like. A substituent of the substituted $C_2$-$C_{60}$ fused polycyclic group may be any one of the substituents presented above where the term "substituted A" is described in more detail.

The unsubstituted $C_1$-$C_{50}$ alkylene group used herein is a linear or branched divalent group of alkane from which two hydrogen atoms are deficient. Examples of the unsubstituted $C_1$-$C_{50}$ alkylene group may be understood by referring to the examples of the unsubstituted $C_1$-$C_{50}$ alkyl group presented above. A substituent of the substituted $C_1$-$C_{50}$ may be any one of the substituents presented above where the term "substituted A" is described in more detail.

The unsubstituted $C_5$-$C_{60}$ arylene used herein refers to a divalent group having a carbocyclic aromatic system having 5 to 60 carbon atoms, and the divalent group may be a monocyclic or polycyclic group. Examples of the unsubstituted $C_5$-$C_{60}$ arylene may be understood by referring to the examples of the unsubstituted $C_5$-$C_{60}$ aryl group. A substituent of the substituted $C_5$-$C_{60}$ arylene may be any one of the substituents presented above where the term "substituted A" is described in more detail.

The unsubstituted $C_5$-$C_{60}$ aryleneoxy group refers to a divalent group wherein a carbon atom of the $C_5$-$C_{60}$ arylene group is attached via an oxygen linker (—O—). A substituent of the substituted $C_5$-$C_{60}$ arylene may be any one of the substituents presented above where the term "substituted A" is described in more detail.

The unsubstituted $C_5$-$C_{60}$ arylenethio group refers to a divalent group wherein a carbon atom of the $C_5$-$C_{60}$ arylene is attached via a sulfur linker (—S—). A substituent of the substitute $C_5$-$C_{60}$ arylenethio group may be any one of the substituents presented above where the term "substituted A" is described in more detail.

The unsubstituted $C_2$-$C_{60}$ heteroarylene group used herein refers to a divalent group that has at least one ring having one or more heteroatoms selected from the group consisting of nitrogen (N), oxygen (O), phosphorous (P), and sulfur (S) and that has 2 to 60 carbon atoms, and may be a monocyclic or polycyclic group. If the unsubstituted $C_2$-$C_{60}$ heteroaryl group is a polycyclic group, two or more rings contained in the unsubstituted $C_2$-$C_{60}$ heteroaryl group may be fused. Examples of the unsubstituted $C_2$-$C_{60}$ heteroarylene group may be understood by referring to the examples of the unsubstituted $C_2$-$C_{60}$ heteroaryl group. A substituent of the substituted $C_2$-$C_{60}$ heteroarylene group may be any one of the substituents presented above where the term "substituted A" is described in more detail.

The organic light-emitting diode including the multi-layered hole transporting layer may include a structure with the following order: a first charge generation layer in which first and second compounds having different energy levels are doped with the first charge generation material having a charge generation capability/a first mixed layer including the first and second compounds/a second charge generation layer in which third and fourth compounds having different energy levels are doped with the second charge generation material having a charge generation capability/a second mixed layer including the third and fourth compounds/a buffer layer/an emission layer.

In this regard, the first compound (or third compound) and the second compound (or fourth compound) may each independently have a triarylamine structure, a carbazole structure, and a fluorene structure, and due to the inclusion of such structures, these compounds have a high glass transition temperature and/or melting point and have stability with respect to injection of electrons. Accordingly, when the organic light-emitting diode is driven and when a hole related layer including the first compound (or third compound) and the second compound (or fourth compound) is interposed between a pair of electrodes of an organic light-emitting diode, the hole related layer may show a strong heat resistance against Joul's heat occurring among organic layers disposed between a pair of electrodes, or between an organic layer and an electrode. Also, the first compound (or third compound) and the second compound (or fourth compound) each essentially have a fluorine ring, and thus, a layer including the compounds may have a high planarization property, and an organic light-emitting diode including the layer may have excellent electrical characteristics. For example, if a mixture including the first compound (or third compound) and the second compound (or fourth compound) is interposed between an emission layer and an anode, deterioration of an organic light-emitting diode due to electrons that migrate through the emission layer may not substantially occur.

Also, in the second compound (or fourth compound), at least one of $R_1$ to $R_5$ is essentially a nitrogen atom-containing group, and due to the nitrogen atom-containing group, hole mobility may be easily controlled. Accordingly, in an organic light-emitting diode including the second compound (or fourth compound), the balance between electrons and holes is increased or maximized due to the nitrogen atom-containing group and thus, luminescence efficiency of the emission layer may be increased. Typically, a hole mobility speed is relatively faster than an electron mobility speed. Accordingly, too many holes reach an emission layer through an anode compared to electrons the reach the emission layer though a cathode, and due to the excess holes, either an exciton formation region in the emission layer may be biased toward the cathode, or an organic layer, such as the emission layer, may deteriorate, and thus the lifetime of an organic light-emitting diode may be reduced. The second compound (or fourth compound), however, has at least one of $R_1$ to $R_5$ being a nitrogen atom-containing group and due to the inclusion of the nitrogen atom-containing group, hole mobility is controlled. Thus, the balance between holes and electrons reaching the emission layer may be increased or maximized, and thus a formed organic light-emitting diode may have a long lifetime. Also, because electrons diffused from the emission layer are stabilized due to the nitrogen atom-containing group in the second compound (or fourth compound), a formed organic light-emitting diode may have a long lifetime.

Also, the nitrogen atom-containing group of the second compound (or fourth compound) is not directly linked to nitrogen located at the center of the chemical structure represented by Formula 2, but is linked to the nitrogen located at the center of the chemical structure represented by Formula 2 through a fluorene ring or $Ar_3$. By doing so, a nitrogen atom-containing group which may be at least one of $R_1$ to $R_5$ may not be directly linked to nitrogen and thus, change in hole related characteristics, such as hole mobility characteristics, may be reduced or prevented, and thus, efficiency of a formed organic light-emitting diode may be improved.

Accordingly, the first mixed layer (or second mixed layer) including a mixture including the second compound (or fourth compound) and the first compound (or third compound) has excellent electrical characteristics, and also in the first mixed layer (or second mixed layer), due to the second compound (or fourth compound), hole mobility is controlled and non-emission quenching occurring near the interface between the emission layer and an adjacent layer to the emission layer is reduced, and thus, the efficiency and lifetime of a formed organic light-emitting diode may be increased.

For example, the organic light-emitting diode may have a structure with the following order: a first electrode/a first charge generation layer/a first mixed layer/a second charge generation layer/a second mixed layer/a buffer layer/an emission layer/an electron transporting layer/an second electrode.

The HOMO energy level of the first compound may be 0.1 eV to 0.2 eV higher than the HOMO energy level of the second compound, and the LUMO energy level of the first compound may be 0.1 eV to 0.2 eV higher than the LUMO energy level of the second compound. If the HOMO and LUMO energy level differences between the first and second compounds are within these ranges, electrons may be trapped without a substantial increase in driving voltage and thus, injected charges may easily migrate and energy transition may easily occur, and a formed device may have improved lifetime characteristics.

For example, the HOMO energy level and the LUMO energy level of the first compound may be from −4.7 to −4.8 eV and from −0.9 to −1.0 eV, respectively, and the HOMO energy level and the LUMO energy level of the second compound may be from −4.8 to −4.9 eV and from −1.0 to −1.1 eV, respectively.

The hole mobility of the first compound may be higher than the hole mobility of the second compound. Due the mixing of the first compound having relatively high hole mobility with the second compound having relatively low hole mobility, hole mobility is controlled and excess charge injection may be reduced or prevented, and thus a formed device may have prolonged lifespan (lifetime).

A mixed weight ratio of the first compound to the second compound may be in a range of 6:4 to 8:2. If the mixed weight ratio of the first compound to the second compound is within this range, hole mobility may be controlled and thus the efficiency and lifetime of a formed device may be increased. A mixed weight ratio of the third compound to the fourth compound may be in a range of 6:4 to 8:2. If the mixed weight ratio of the third compound to the second compound is within this range, hole mobility may be controlled and thus the efficiency and lifetime of a formed device may be increased.

A thickness of each of the first mixed layer and the second mixed layer may be in a range of 40 nm to 60 nm. If the thicknesses of the first mixed layer and the second mixed layer are within this range, hole mobility may be appropriately (suitably) controlled without a substantial increase in driving voltage.

An amount of the first charge generation material may be in a range of 1 to 3 parts by weight based on 100 parts by weight of the first charge generation layer. The first charge generation material is a material for generating charges, and may be homogeneously dispersed or non-homogeneously distributed in the first charge generation layer. However, the distribution of the first charge generation material in the first charge generation layer may not be limited to the above disclosure. If the amount of the first charge generation material is within this range, an appropriate (suitable) amount of charge may be generated in the first charge generation layer.

An amount of the second charge generation material may be in a range of 1 to 3 parts by weight based on 100 parts by weight of the second charge generation layer. The second charge generation material may be homogeneously dispersed or non-homogeneously distributed in the second charge generation layer. However, the distribution of the second charge generation material in the second charge generation layer may not be limited to the above disclosure. If the amount of the second charge generation material is within this range, an appropriate (suitable) amount of charge may be generated in the second charge generation layer.

A thickness of each of the first charge generation layer and the second charge generation layer may be in a range of 10 nm to 20 nm. If the thicknesses of the first charge generation layer and the second charge generation layer are within this range, an appropriate (suitable) amount of charge may be generated without a substantial increase in driving voltage.

A buffer layer may be interposed between the emission layer and the second mixed layer. If the emission layer directly contacts the second mixed layer, the second mixed layer may attract electrons and thus, the lifetime of the emission layer may be reduced. Accordingly, the insertion of the buffer layer between the emission layer and the second mixed layer may prevent or reduce the attracting of electrons, thereby contributing to improved lifetime. Also, the buffer layer may compensate an optical resonance distance according to a wavelength of light emitted from the emission layer, thereby improving efficiency of a formed organic light-emitting diode.

The buffer layer may include the compound represented by Formula 1 having excellent hole mobility, but is not limited thereto. For example, as a material for forming a buffer layer, a mixed material including the first compound and a light emission host material may be used. In this case, a HOMO energy level of the buffer layer may be present between the HOMO energy level of the second mixed layer and the HOMO energy level of the emission layer, and thus holes may be easily transported.

A thickness of the buffer layer may be in a range of 0.1 nm to 30 nm. If the thickness of the buffer layer is within this range, the efficiency of a formed organic light-emitting diode may be increased due to the compensation of an optical resonance distance according to a wavelength of light emitted from the emission layer without a substantial increase in driving voltage.

The first mixed layer may contact the first charge generation layer. If the first mixed layer contacts the first charge generation layer, a charge balance may be improved.

The second mixed layer may contact the second charge generation layer. If the second mixed layer contacts the second charge generation layer, a charge balance may be improved.

An organic light-emitting diode according to an embodiment of the present invention may include at least one layer of a hole blocking layer, an electron transporting layer, an electron injection layer, and a functional layer having an electron transport function and an electron injection function, which are interposed between the emission layer and the second electrode.

For example, the organic light-emitting diode may have a structure with the following order: a first electrode/a first charge generation layer in which first and second compounds having different energy levels are doped with the first charge generation material/a first mixed layer including the first and second compounds/second charge generation layer in which third and fourth compounds having different energy levels are doped with the second charge generation material/a second mixed layer including the third and fourth compounds/a buffer layer/an emission layer/an electron transporting layer/an electron injection layer/a second electrode.

FIG. 1 is a schematic view of an organic light-emitting diode 100 according to an embodiment of the present invention. Hereinafter, with reference to FIG. 1, the structure of an organic light-emitting diode according to an embodiment of the present invention, and a method of manufacturing the organic light-emitting diode, according to an embodiment of the present invention, will be described in more detail.

The organic light-emitting diode 100 sequentially includes a substrate 110, a first electrode 120, a hole injection layer 130, a first charge generation layer 141, a first mixed layer 142, a second charge generation layer 143, a second mixed layer 144, a buffer layer 150, an emission layer 160, an electron transporting layer 170, an electron injection layer 180, and a second electrode 190 in this stated order.

The substrate 110 may be any one of various suitable substrates that are used in an organic light-emitting device, and may be a glass substrate or a transparent plastic substrate with excellent mechanical strength, thermal stability, transparency, surface smoothness, ease of handling, and water repellency.

The first electrode 120 may be formed by providing a first electrode material on a substrate by deposition or sputtering. If the first electrode 120 is an anode, to allow holes to be injected thereinto easily, the first electrode material may be selected from materials having a high work function. Also, the first electrode 120 may be a reflection electrode or a transmission electrode. The first electrode material may be a transparent and highly conductive material, such as indium tin oxide (ITO), indium zinc oxide (IZO), tin oxide ($SnO_2$), zinc oxide (ZnO), etc. Alternatively, if magnesium (Mg), aluminum (Al), aluminum-lithium (Al—Li), calcium (Ca), magnesium-indium (Mg—In), magnesium-silver (Mg—Ag), etc., are used as the first electrode material, the first electrode 120 may be formed as a reflection electrode. The first electrode 120 may include two different materials. For example, the first electrode 120 may have a two-layer structure including two different materials. However, the structure of the first electrode 120 is not limited thereto.

The hole injection layer 130 is formed on the first electrode 120. However, according to purpose, the hole injection layer 130 may not be formed.

The hole injection layer 130 may be formed on the first electrode 120 by using various suitable methods, such as vacuum deposition, wet process, laser transferring, etc., as described above.

When the hole injection layer 130 is formed by vacuum deposition, the deposition conditions may vary according to a material that is used to form the hole injection layer 130, and the structure and thermal characteristics of the hole injection layer 130. For example, the deposition conditions may include a deposition temperature of about 100° C. to about 500° C., a vacuum pressure of about $10^{-8}$ to about $10^{-3}$ torr, and a deposition rate of about 0.01 Å/sec to about 100 Å/sec. However, the deposition conditions are not limited thereto.

When the hole injection layer 130 is formed using spin coating as a wet process, coating conditions may vary according to the material used to form the hole injection layer 130, and according to the structure and thermal properties of the hole injection layer 130. For example, a coating speed may be from about 2000 rpm to about 5000 rpm, and a temperature at which a heat treatment is performed to remove a solvent after coating may be from about 80° C. to about 200° C. However, the coating conditions are not limited thereto.

A hole injection layer material may be any one of known hole injecting materials. Non-limiting examples of the hole injection layer material are a phthalocyanine compound, such as copperphthalocyanine, m-MTDATA (a structure thereof is illustrated below), TDATA (a structure thereof is illustrated below), 2-TNATA (a structure thereof is illustrated below), polyaniline/dodecylbenzenesulfonic acid (Pani/DBSA), poly (3,4-ethylenedioxythiophene)/poly(4-styrenesulfonate) (PEDOT/PSS), polyaniline/camphor sulfonic acid (Pani/CSA), polyaniline/poly(4-styrenesulfonate) (Pani/PSS), etc.

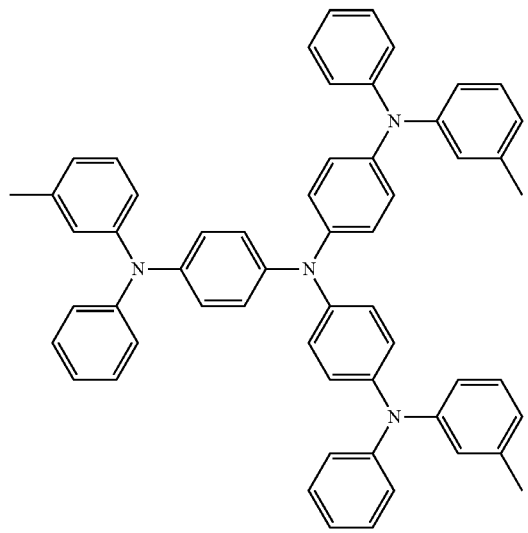

m-MTDATA

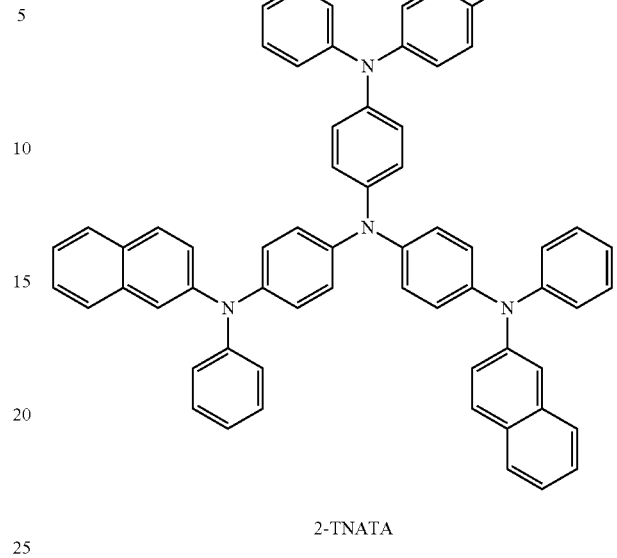

2-TNATA

The hole injection layer 130 may have a thickness of about 100 Å to about 10,000 Å, for example, a thickness of about 100 Å to about 1,000 Å. When the thickness of the hole injection layer 130 is within these ranges, the hole injection layer 130 may have satisfactory hole injection characteristics without an increase in driving voltage.

Then, a hole transporting layer 140 may be formed on the hole injection layer 130. The hole transporting layer 140 may include the first charge generation layer 141, the first mixed layer 142, the second charge generation layer 143, and the second mixed layer 144 which are sequentially deposited in this stated order.

First, the first charge generation layer 141 may be formed on the hole injection layer 130 by vacuum deposition, wet process, laser transferring, or the like. When the first charge generation layer 141 is formed by vacuum deposition or spin coating, the deposition or coating conditions may be similar to those applied to form the hole injection layer 130, although the deposition or coating conditions may vary according to the material that is used to form the first charge generation layer 141.

As a material for forming the first charge generation layer 141, a mixture including a first compound and a second compound, doped with a first charge generation material, may be used. In this regard, a weight ratio of the first compound and the second compound may be in a range of 6:4 to 8:2 and an amount of the first charge generation material may be in a range of 1 to 3 parts by weight based on 100 parts by weight of the first charge generation layer 141.

A thickness of the first charge generation layer 141 may be in a range of 10 nm to 20 nm. If the thickness of the first charge generation layer 141 is within this range, the first charge generation layer 141 may have satisfactory hole transport characteristics and a sufficient amount of charge without a substantial increase in driving voltage.

The first mixed layer 142 may be formed on the first charge generation layer 141 by, for example, vacuum deposition, wet process, or laser transferring. When the first mixed layer 142 is formed by vacuum deposition or spin coating, the deposition or coating conditions may be similar to those applied to form the hole injection layer 130, although the deposition or

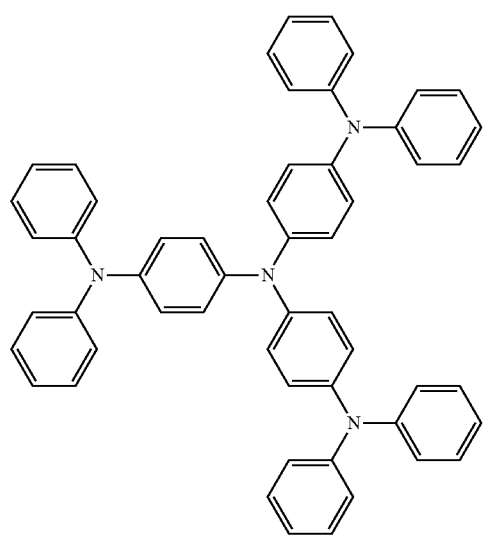

TDATA coating conditions may vary according to the material that is used to form the first mixed layer 142.

As a material for forming the first mixed layer 142, a mixture including a first compound and a second compound may be used. In this regard, a weight ratio of the first compound to the second compound may be in a range of 6:4 to 8:2.

A thickness of the first mixed layer 142 may be in a range of 40 nm to 60 nm. If the thickness of the first mixed layer 142 is within this range, the first mixed layer 142 may have satisfactory hole transport characteristics and hole mobility without a substantial increase in driving voltage.

The second charge generation layer 143 may be formed on the first mixed layer 142 by, for example, vacuum deposition, wet process, or laser transferring. When the second charge generation layer 143 is formed by vacuum deposition or spin coating, the deposition or coating conditions may be similar to those applied to form the hole injection layer 130, although the deposition or coating conditions may vary according to the material that is used to form the second charge generation layer 143.

As a material for forming the second charge generation layer 143, a mixture including a third compound and a fourth compound, doped with a second charge generation material, may be used. In this regard, a weight ratio of the third compound to the fourth compound may be in a range of 6:4 to 8:2 and an amount of the second charge generation layer material may be in a range of 1 to 3 parts by weight based on 100 parts by weight of the second charge generation layer.

A thickness of the second charge generation layer 143 may be in a range of 10 nm to 20 nm. If the amount of the second charge generation layer 143 is within this range, the second charge generation layer 143 may have satisfactory hole transport characteristics and a sufficient amount of charge without a substantial increase in driving voltage.

The second mixed layer 144 may be formed on the second charge generation layer 143 by, for example, vacuum deposition, wet process, or laser transferring. When the second mixed layer 144 is formed by vacuum deposition or spin coating, the deposition or coating conditions may be similar to those applied to form the hole injection layer 130, although the deposition or coating conditions may vary according to the material that is used to form the second mixed layer 144.

As a material for forming the second mixed layer 144, In this regard, a weight ratio of the third compound to the fourth compound may be in a range of 6:4 to 8:2.

A thickness of the second mixed layer 144 may be in a range of 40 nm to 80 nm. If the thickness of the second mixed layer 144 is within this range, the second mixed layer 144 may have satisfactory hole transport characteristics and hole mobility without a substantial increase in driving voltage.

The buffer layer 150 may be formed on the second mixed layer 144 by, for example, vacuum deposition, wet process, or laser transferring. When the buffer layer 150 is formed by vacuum deposition or spin coating, the deposition or coating conditions may be similar to those applied to form the hole injection layer 130, although the deposition or coating conditions may vary according to the material that is used to form the buffer layer 150.

A material for forming the buffer layer 150 may be the first compound. According to an embodiment of the present invention, a mixture including the first compound and a luminescent host material may be used as the buffer layer forming material.

A thickness of the buffer layer 150 may be in a range of 0.1 nm to 30 nm. If the thickness of the buffer layer 150 is within this range, a driving voltage may not be excessively increased, and due to the compensation for an optical resonance distance according to a wavelength of light emitted from the emission layer 160, efficiency of a formed organic light-emitting diode may be improved.

The emission layer 160 may be formed on the buffer layer 150 by, for example, vacuum deposition, wet process, or laser transferring. When the emission layer 160 is formed by vacuum deposition or spin coating, the deposition or coating conditions may be similar to those applied to form the hole injection layer 130, although the deposition or coating conditions may vary according to the material that is used to form the emission layer 160.

The emission layer 160 may include a known phosphorescent host, a fluorescent host, a phosphorescent dopant, or a fluorescent dopant. As a known host, 4,4'-N,N'-dicarbazole-biphenyl (CBP), 9,10-di-naphthalene-2-yl-anthracene (AND, a structure thereof is illustrated below), TPBI (a structure thereof is illustrated below), TBADN (a structure thereof is illustrated below), E3 (a structure thereof is illustrated below), etc. may be used, but are not limited thereto.

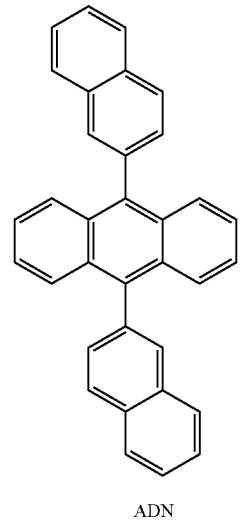

ADN

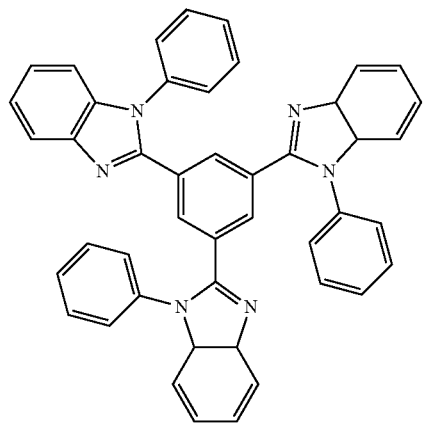

TPBI

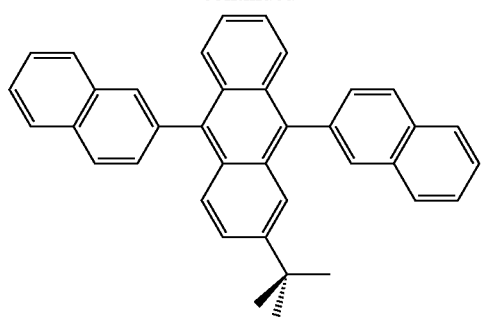

TBADN

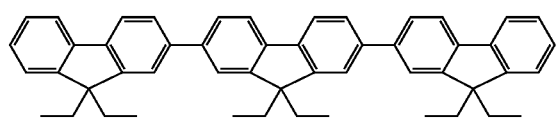

E3

As a red dopant, PtOEP (a structure thereof is illustrated below), Ir(piq)$_3$ (a structure thereof is illustrated below), Btp$_2$Ir(acac) (a structure thereof is illustrated below), etc. may be used, but are not limited thereto.

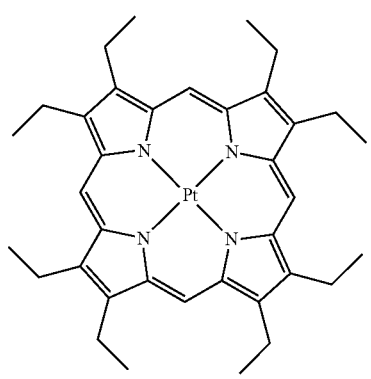

PtOEP

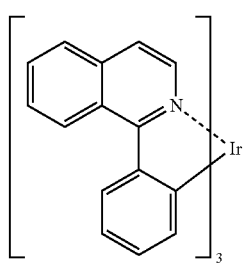

Ir(piq)$_3$

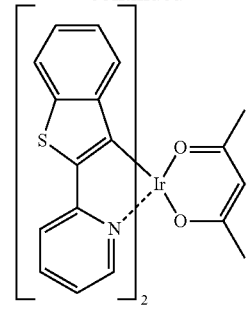

Btp$_2$Ir(acac)

Also, as a green dopant, Ir(ppy)$_3$ (ppy=phenyl pyridine, a structure thereof is illustrated below), Ir(ppy)$_2$(acac) (a structure thereof is illustrated below), Ir(mpyp)$_3$ (a structure thereof is illustrated below), etc. may be used, but are not limited thereto.

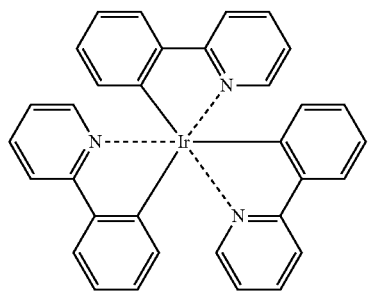

Ir(ppy)$_3$

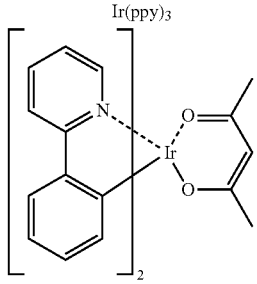

Ir(ppy)$_2$(acac)

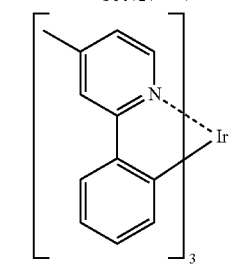

Ir(mpyp)$_3$

As a blue dopant, F$_2$Irpic (a structure thereof is illustrated below), (F$_2$ppy)$_2$Ir(tmd) (a structure thereof is illustrated below), Ir(dfppz)$_3$ (a structure thereof is illustrated below), DPVBi (a structure thereof is illustrated below), 4,4'-bis(4-diphenyl aminostaryl)biphenyl (DPAVBi, a structure thereof is illustrated below), 2,5,8,11-tetra-tert-butyl perylene (TBPe, a structure thereof is illustrated below), etc. may be used, but are not limited thereto.
If the emission layer 160 includes a host and a dopant, an amount of the dopant may be from about 0.01 to about 15
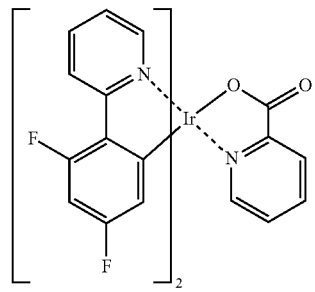
F₂Irpic
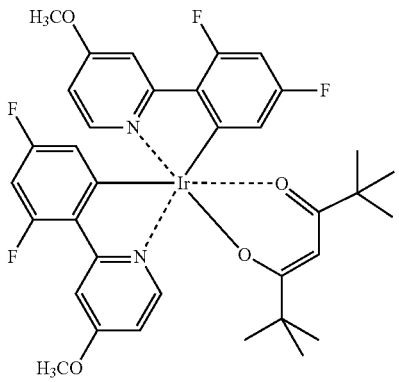
(F₂ppy)₂Ir(tmd)
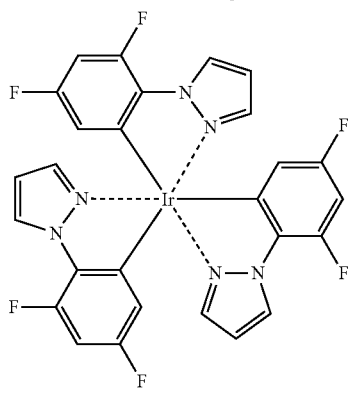
Ir(dfppz)₃
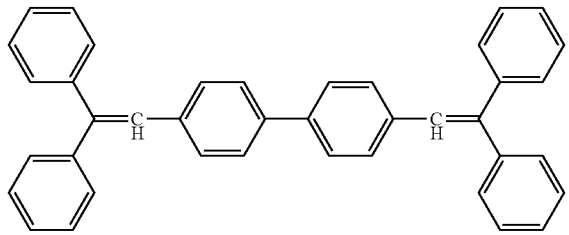
DPVBi
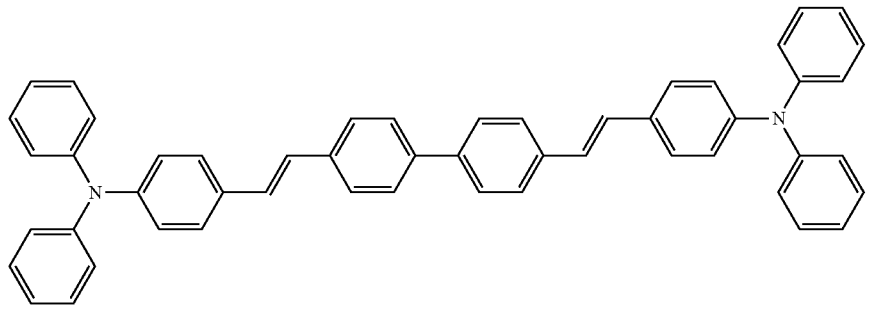
DPAVBi
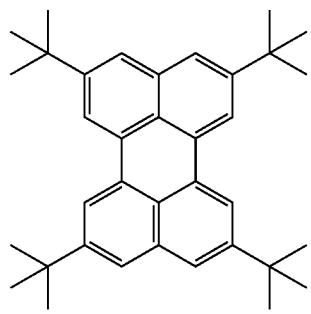
TBPe parts by weight based on about 100 parts by weight of the host, but are not limited thereto.

A thickness of the emission layer 160 may be from about 100 Å to about 1000 Å, for example, about 200 Å to about 600 Å. If the thickness of the emission layer 160 is within these ranges, excellent luminescence characteristics may be obtained without a substantial increase in driving voltage.

If the emission layer 160 includes a phosphorescent dopant, to prevent diffusion of a triple exciton or a hole into the electron transporting layer 170, a hole blocking layer (HBL, not shown in FIG. 1) may be formed between the electron transporting layer 170 and the emission layer 160 by vacuum deposition, wet process, or laser transferring. If the HBL is formed by vacuum deposition or spin coating, the deposition or coating conditions may be similar to those applied to form the hole injection layer 130, although the deposition or coating conditions may vary according to the material that is used to form the HBL. As an HBL material, any one of known hole blocking materials may be used, and examples thereof are an oxadiazole derivative, a triazole derivative, a phenanthroline derivative, etc.

A thickness of the HBL may be from about 50 Å to about 1000 Å, for example, about 100 Å to about 300 Å. If the thickness of the HBL is within the ranges described above, excellent hole blocking characteristics may be obtained without a substantial increase in driving voltage.

Then, the electron transporting layer 170 may be formed by using various methods, such as vacuum deposition, wet process, laser transferring, etc., as described above. The electron transporting layer may include a known electron transport material. Non-limiting examples of the known electron transport material are a quinoline derivative, such as tris(8-quinolinolate)aluminum (Alq$_3$), TAZ (a structure thereof is illustrated below), BAlq (a structure thereof is illustrated below), and beryllium bis(benzoquinolin-10-olate (Bebq$_2$).

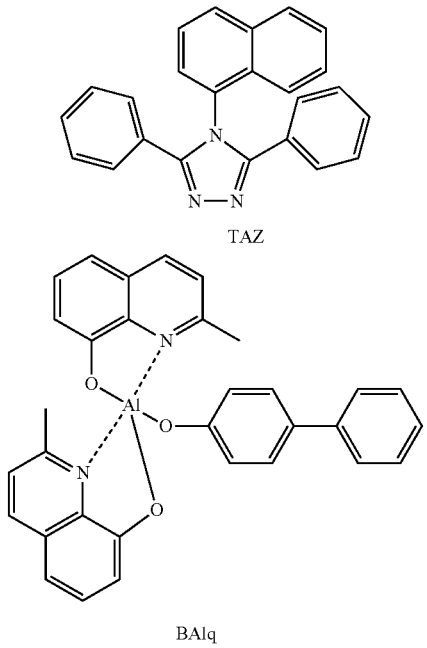

TAZ

BAlq

The electron transporting layer 170 may include an electron transportable organic compound. Non-limiting examples of the electron transportable organic compound are 9,10-di(naphthalene-2-yl)anthracene (ADN); and anthracene-based compounds, such as Compounds 601 and 602 below:

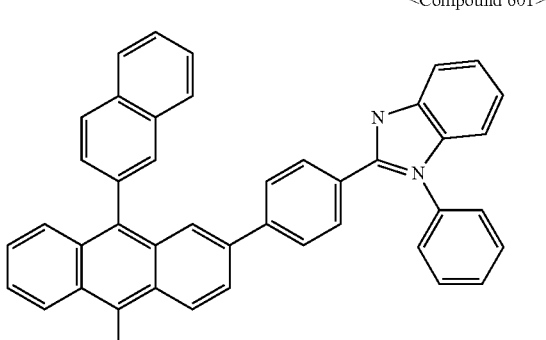
<Compound 601>

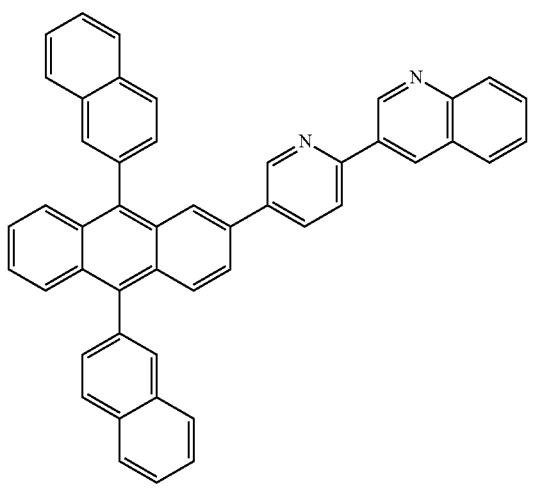
<Compound 602>

A thickness of the electron transporting layer 170 may be from about 100 Å to about 1000 Å, for example, about 150 Å to about 500 Å. If the thickness of the electron transporting layer 170 is within the ranges described above, excellent electron transporting characteristics may be obtained without a substantial increase in driving voltage. If the electron transporting layer 170 is formed by vacuum deposition or spin coating, the deposition or coating conditions may be similar to those applied to form the hole injection layer 130, although the deposition or coating conditions may vary according to the material that is used to form the electron transporting layer 170.

The electron injection layer 180 may be deposited on the electron transporting layer 170 by using a material that allows electrons to be easily injected from an anode. As a material for forming the electron injection layer 180, any known electron injection layer material, such as LiF, NaCl, CsF, Li$_2$O, BaO, or LIQ, may be used. Alternatively, the heterocyclic compound of Formula 1 may also be used. The deposition conditions of the electron injection layer 180 may be similar to those applied to form the hole injection layer 130, although the deposition or coating conditions may vary according to the material that is used to form the electron injection layer 180.

A thickness of the electron injection layer 180 may be in a range of about 1 Å to about 100 Å, for example, about 3 Å to about 90 Å. If the thickness of the electron injection layer 180 is within the ranges described above, excellent electron injection characteristics may be obtained without a substantial increase in driving voltage.

The second electrode 190 is formed as a reflection electrode on the electron injection layer 180. The second electrode 190 may be a cathode as an electron injection electrode, and in this case, a low work function metal, alloy, electrically conductive compound, and a mixture thereof may be used as a second electrode metal. In detail, lithium (Li), magnesium (Mg), aluminum (Al), aluminum-lithium (Al—Li), calcium (Ca), magnesium-indium (Mg—In), magnesium-silver (Mg—Ag), etc. may be formed as a thin film for use as a reflection electrode. Also, if the organic light-emitting diode is used in a top-emission light-emitting device, a transmission electrode may be formed using ITO or IZO.

Hereinbefore, the organic light-emitting diode has been described with reference to FIG. 1. However, the structure of the organic light-emitting diode is not limited to the structure illustrated in FIG. 1.

Figure 2:
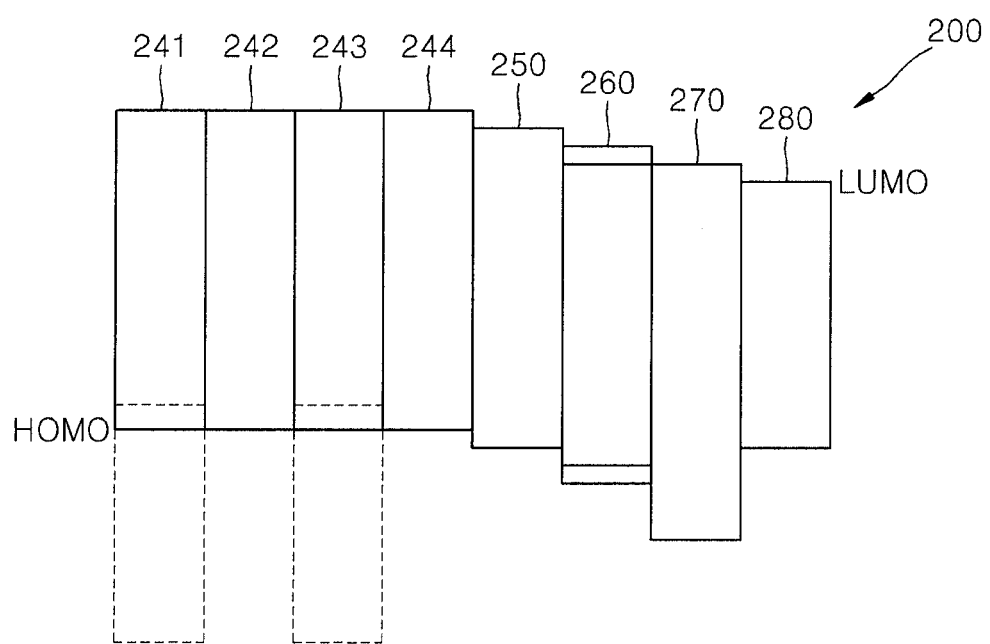
FIG. 2 shows energy levels of an organic light-emitting diode according to an embodiment of the present invention.

FIG. 2 shows energy levels of an organic light-emitting diode 200 according to an embodiment of the present invention.

The organic light-emitting diode may include a first charge generation layer 241, a first mixed layer 242, a second charge generation layer 243, a second mixed layer 244, a buffer layer 250, an emission layer 260, an electron transporting layer 270, and an electron injection layer 280. Because the first charge generation layer 241 includes a first compound, a second compound, and a first charge generation material, and the second charge generation layer 243 includes a third compound, a fourth compound, and a second charge generation material, the first and second charge generation layers 241 and 243 may have similar levels of HOMO energy and LUMO energy. The first and second charge generation layers 241 and 243 include a first charge generation material and a second charge generation material, respectively, and a HOMO energy level and a LUMO energy level thereof are indicated by a dotted line. The HOMO and LUMO energy levels of each of the first and second charge generation materials are relatively very low, the first and second charge generation materials may contribute to a decrease in a driving voltage of the first charge generation layer 241 and the second charge generation layer 243.

The first mixed layer 242 includes a first compound and a second compound, and the second mixed layer 244 includes a third compound and a fourth compound, and the first and second mixed layers 242 and 244 have similar levels of HOMO energy and LUMO energy.

The organic light-emitting diode may be included in a flat display device including a transistor. Accordingly, another aspect of the present invention provides a flat display device that includes: a transistor including a source, a drain, a gate, and an active layer; and the organic light-emitting diode (including the multi-layered hole transporting layer), wherein the first electrode of the organic light-emitting diode is electrically connected to the source or the drain.

Figure 4:
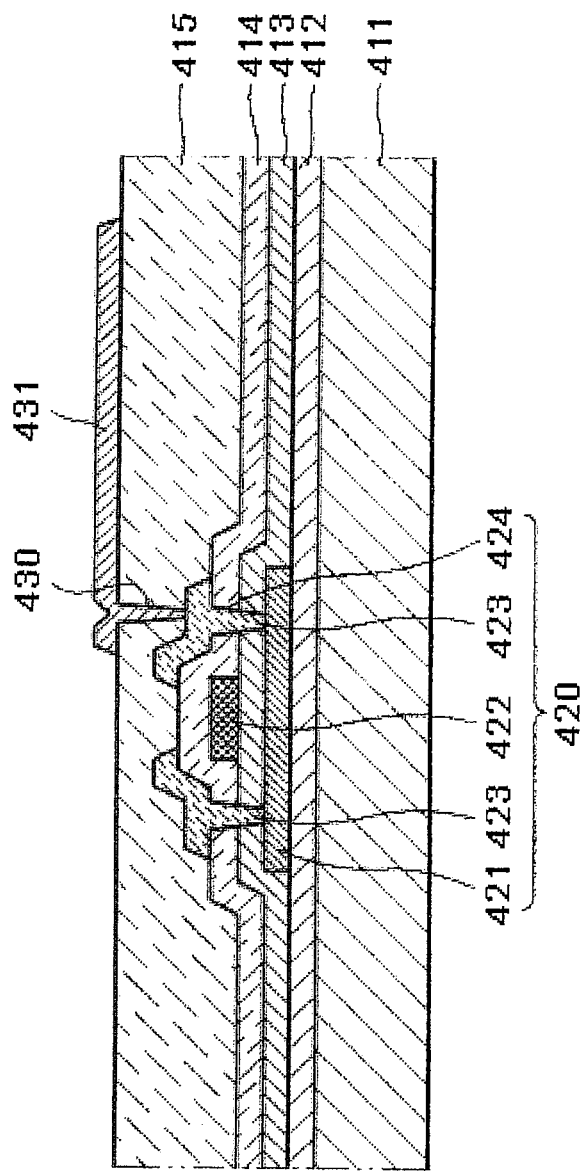
FIG. 4 is a cross-sectional view of an embodiment of a flat display device.

According to embodiments of the present invention, as shown in FIG. 4, a flat display device includes a driving circuit 420 electrically connected to a pixel unit on a substrate 411. An insulating layer 412 such as a barrier layer and/or a buffer layer may be formed on the substrate 411 to planarize the surface of the substrate and to substantially prevent the diffusion of impurities and the penetration of external moisture and air. A transistor as the driving circuit 420 is formed on the insulating layer 412. According to some embodiments, a top gate TFT may be used. However, it is understood that various other types of transistors may also be used. An activation layer 421 of the transistor includes a semiconductor material and is disposed on the insulating layer 412. A gate insulating layer 413 covers the activation layer 421. The activation layer 421 may include inorganic semiconductor materials (such as amorphous silicon or polysilicon), or organic semiconductor materials, and may have a source region, a drain region, and a channel region between the source region and the drain region. A gate electrode 422 is disposed on the gate insulating layer 413, and an interlayer insulating layer 414 covers the gate electrode 422. Source and drain electrodes 423 are disposed on the interlayer insulating layer 414 and contact the activation layer through contact holes 424. A planarization layer 415 covers the source and drain electrodes 423. It is understood that the stack structure of the transistor is not limited to this constructions, but rather the transistor may have any suitable structure. The first electrode 431 of the organic light emitting device is formed on the planarization layer 415, and is electrically connected to the source and drain electrodes 423 via a through hole 430. A pixel definition layer (not shown) is a thin inorganic layer formed on the first electrode 431. An opening is formed in the pixel definition layer to expose the first electrode 431 through the opening.

The active layer of the transistor may be, for example, an amorphous silicon layer, a crystalline silicon layer, an organic semiconductor layer, an oxide semiconductor layer, or the like.

Hereinafter, an organic light-emitting diode according to an embodiment of the present invention will be described in detail with reference to Examples. However, the present invention is not limited to Examples below.

Example 1

As an anode, 15 Ω/cm$^2$(1200 Å) ITO glass substrate manufactured by Corning Co., Ltd was cut to a size of 50 mm×50 mm×0.7 mm and sonicated with isopropyl alcohol and pure water each for 5 minutes, and then an ultraviolet ray was irradiated thereto for 30 minutes, followed by exposure to ozone. Then, the resultant ITO glass substrate was installed in a vacuum deposition device.

Compound 301, Compound 35, and Compound 502 were vacuum co-deposited at a weight ratio of 60:40:1 on the ITO glass substrate to form a first charge generation layer having a thickness of 100 Å, and then Compound 301 and Compound 35 were vacuum co-deposited at a weight ratio of 60:40 on the first charge generation layer to form a first mixed layer having a thickness of 400 Å. Then, Compound 301, Compound 35, and Compound 502 were vacuum co-deposited at a weight ratio of 60:40:1 on the first mixed layer to form a second charge generation layer having a thickness of 100 Å, and then Compound 301 and Compound 35 were vacuum co-deposited at a weight ratio of 60:40 on the second charge generation layer to form a second mixed layer having a thickness of 400 Å.

Compound 301 was vacuum deposited on the second mixed layer to form a buffer layer having a thickness of 230 Å.

ADN and DPVBi were vacuum co-deposited at a weight ratio of 98:2 on the buffer layer to form an emission layer having a thickness of 300 Å.

Then, Alq$_3$ was vacuum deposited on the emission layer to form an electron transporting layer having a thickness of 300 Å.

LiF, which is a halogenated alkali metal, was vacuum deposited on the electron transporting layer to form an electron injection layer having a thickness of 10 Å, followed by vacuum deposition of Al thereon to a thickness of 3000 Å (cathode), to form an LiF/Al electrode, thereby completing the manufacture of an organic light-emitting diode.

Example 2

An organic light-emitting diode was manufactured in the same manner as in Example 1, except that when the first charge generation layer and the second charge generation layer were formed, Compound 301, Compound 35, and Compound 502 were used at a weight ratio of 70:30:1, and when the first mixed layer and the second mixed layer were formed, Compound 301 and Compound 35 were used at a weight ratio of 70:30.

Example 3

An organic light-emitting diode was manufactured in the same manner as in Example 1, except that when the first charge generation layer and the second charge generation layer were formed, Compound 301, Compound 35, and Compound 502 were used at a weight ratio of 70:30:3, and when the first mixed layer and the second mixed layer were formed, Compound 301 and Compound 35 were used at a weight ratio of 70:30.

Example 4

An organic light-emitting diode was manufactured in the same manner as in Example 1, except that when the first charge generation layer and the second charge generation layer were formed, Compound 301, Compound 35, and Compound 502 were used at a weight ratio of 80:20:1, and when the first mixed layer and the second mixed layer were formed, Compound 301 and Compound 35 were used at a weight ratio of 80:20.

Comparative Example 1

An organic light-emitting diode was manufactured in the same manner as in Example 2, except that the buffer layer was not formed.

Comparative Example 2

An organic light-emitting diode was manufactured in the same manner as in Example 1, except that instead of the forming of the first charge generation layer, the first mixed layer, the second charge generation layer, and the second mixed layer, 2-TNATA was vacuum deposited on the ITO glass substrate to form a single hole injection layer having a thickness of 600 Å.

Evaluation Example

The driving voltage, y value of CIE chromaticity diagram, luminescent efficiency, and lifespan (lifetime) of the organic light-emitting diodes manufactured according to Examples 1 to 4 and Comparative Examples 1 to 2 were evaluated by using a PR650 (Spectroscan) source measurement unit (product of PhotoResearch Company), and results thereof are shown in Table 1 below.

TABLE 1

|  | Driving Voltage (V) | CIE_y | Efficiency/y | Half lifetime (hr@100 mA/cm$^2$) |
|---|---|---|---|---|
| Example 1 | 5.9 | 0.062 | 106.1 | 59.0 |
| Example 2 | 5.6 | 0.057 | 95.3 | 68.0 |
| Example 3 | 5.2 | 0.050 | 97.9 | 76.0 |
| Example 4 | 5.3 | 0.050 | 100.4 | 56.0 |
| Comparative Example 1 | 5.2 | 0.057 | 98.0 | 6.0 |
| Comparative Example 2 | 5.2 | 0.052 | 72.8 | 26.0 |

Referring to Table 1, an organic light-emitting diode according to an embodiment of the present invention (Examples 1 to 4) has a longer lifetime than an organic light-emitting diode (Comparative Examples 1 to 2) including a hole transporting layer in which a buffer layer was not formed or which did not have a multi-layered structure.

Figure 3:
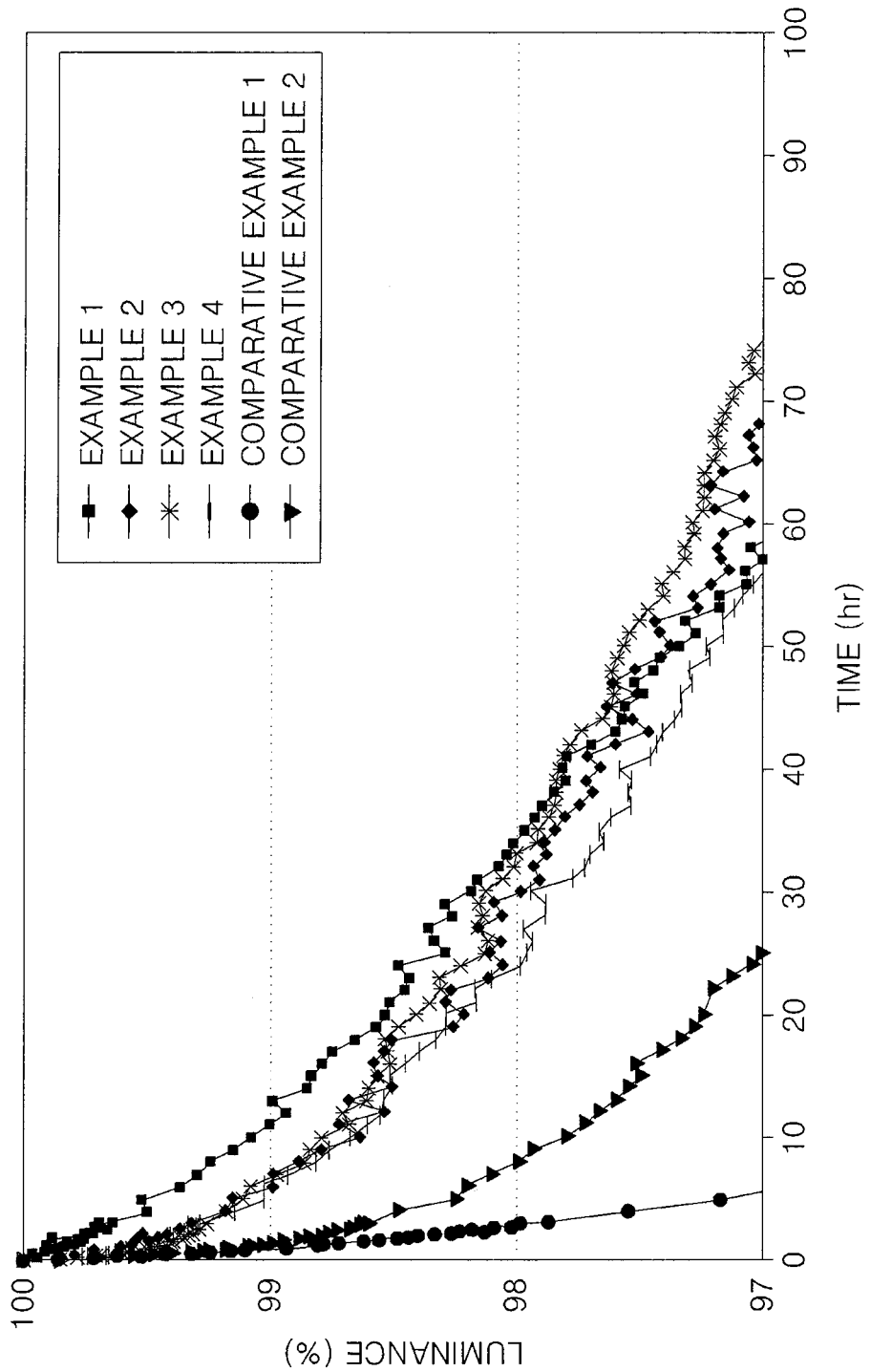
FIG. 3 is a graph of lifetime characteristics of organic light-emitting diodes manufactured according to Examples 1 to 4 and organic light-emitting diodes manufactured according to Comparative Examples 1 and 2.

FIG. 3 is a graph of lifetime characteristics of the organic light-emitting diodes manufactured according to Examples 1 to 4 and organic light-emitting diodes manufactured according to Comparative Examples 1 and 2. Referring to FIG. 3, it was confirmed that an organic light-emitting diode according to an embodiment of the present invention (Examples 1 to 4) had about 3 to 12 times greater lifetime than an organic light-emitting diode (Comparative Examples 1 to 2) including a hole transporting layer in which a buffer layer was not formed or which did not have a multi-layered structure.

Referring to Table 1, it was confirmed that an organic light-emitting diode according to an embodiment of the present invention (Examples 1 to 4) had about 30% greater luminescence efficiency than an organic light-emitting diode (Comparative Example 2) including a hole transporting layer which did not have a multi-layered structure.

An organic light-emitting diode according to an embodiment of the present invention has improved charge balance, high efficiency, and long lifetime characteristics due to the inclusion of a multi-layered hole transporting layer including a combination of a hole transporting compound and a charge generation material having different energy levels.

While the present invention has been particularly shown and described with reference to exemplary embodiments thereof, it will be understood by those of ordinary skill in the art that various changes in form and details may be made therein without departing from the spirit and scope of the present invention as defined by the following claims, and equivalents thereof.

What is claimed is:
1. An organic light-emitting diode comprising:
a first electrode;
a second electrode facing the first electrode;
an emission layer between the first electrode and the second electrode;
a first mixed layer between the emission layer and the first electrode and comprising a first compound and a second compound;
a second mixed layer between the emission layer and the first mixed layer and comprising a third compound and a fourth compound;

a first charge generation layer between the first mixed layer and the first electrode and comprising the first compound, the second compound, and a first charge generation material;
a second charge generation layer between the first mixed layer and the second mixed layer and comprising the third compound, the fourth compound, and a second charge generation material; and
a buffer layer between the emission layer and the second mixed layer,
wherein the first compound and the third compound are each independently a compound represented by Formula 1 below, and the second compound and the fourth compound are each independently a compound represented by Formula 2 below:

<Formula 1>

[structure of Formula 1 shown]

wherein in Formula 1,
$Ar_{11}$ and $Ar_{12}$ are each independently a substituted or unsubstituted $C_6$-$C_{60}$ arylene group;
e and f are each independently an integer of 0 to 5;
$R_{51}$ to $R_{58}$ and $R_{61}$ to $R_{69}$ are each independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or substituted or unsubstituted $C_6$-$C_{60}$ arylthio group; and
$R_{59}$ is a phenyl group, a naphthyl group, an anthryl group, a biphenyl group, or a pyridyl group or is a phenyl group, a naphthyl group, an anthryl group, a biphenyl group, or a pyridyl group, of which at least one hydrogen atom is each independently substituted with a deuterium atom; a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{20}$ alkyl group, or a substituted or unsubstituted $C_1$-$C_{20}$ alkoxy; and

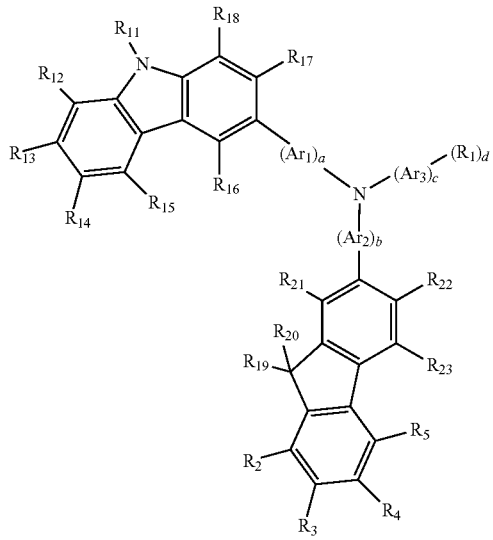

<Formula 2> wherein in Formula 2,
$Ar_1$ to $Ar_a$ are each independently a substituted or unsubstituted $C_6$-$C_{60}$ arylene group;
a and b are each independently an integer of 0 to 5;
c is an integer of 1 to 5;
$R_1$ to $R_5$ are each independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof; phosphoric acid group or salt thereof; a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, —Si($R_{31}$)($R_{32}$)($R_{33}$), —N($R_{34}$)($R_{35}$), or a nitrogen atom-containing group, and at least one of $R_1$ to $R_5$ is a nitrogen atom-containing group;
d is an integer of 0 to 5;
$R_{11}$ to $R_{23}$ are each independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, —Si($R_{36}$)($R_{37}$)($R_{38}$), or —N($R_{39}$)($R_{40}$); and $R_{31}$ to $R_{40}$ are each independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group;

wherein the nitrogen atom-containing group is a 5-membered aromatic ring group comprising a nitrogen atom as a ring atom, a 6-membered aromatic ring group comprising a nitrogen atom as a ring atom, or a 9-membered aromatic ring group comprising a nitrogen atom as a ring atom and is formed by fusing a 5-membered aromatic group and a 6-membered aromatic group.

2. The organic light-emitting diode of claim 1, wherein a highest occupied molecular orbital (HOMO) energy level of the second compound is 0.1 eV to 0.2 eV lower than a HOMO energy level of the first compound, and a lowest unoccupied molecular orbital (LUMO) energy level of the second compound is 0.1 eV to 0.2 eV lower than a LUMO energy level of the first compound.

3. The organic light-emitting diode of claim 1, wherein a hole mobility of the first compound is higher than a hole mobility of the second compound.

4. The organic light-emitting diode of claim 1, wherein the first compound and the third compound are each independently a compound represented by Formula 1A:

<Formula 1A>

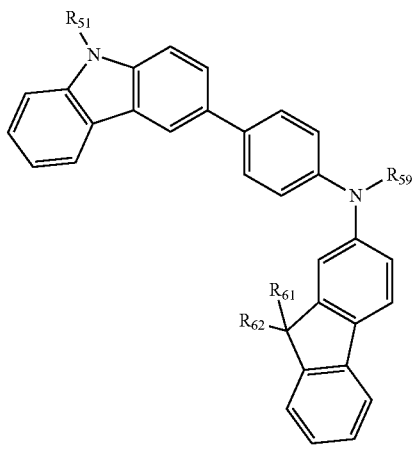

wherein in Formula 1A, $R_{51}$, $R_{59}$, $R_{61}$, and $R_{62}$ are the same as with respect to Formula 1.

5. The organic light-emitting diode of claim 1, wherein the first compound and the third compound are each independently Compound 301 below:

<Compound 301>

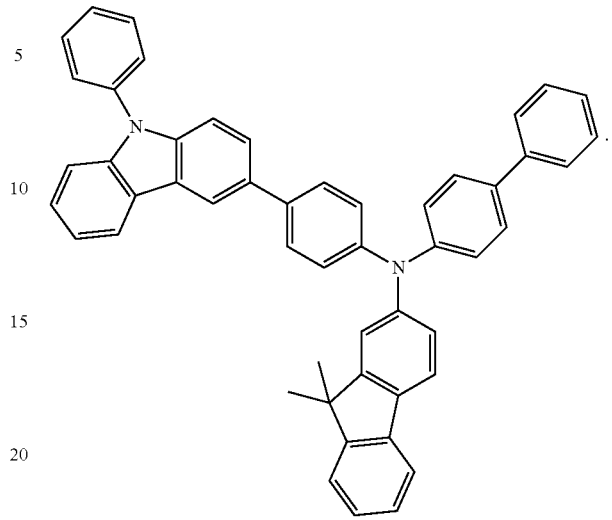

6. The organic light-emitting diode of claim 1, wherein the second compound and the fourth compound are each independently at least one of compounds represented by Formulae 2A to 2K below:

<Formula 2A>

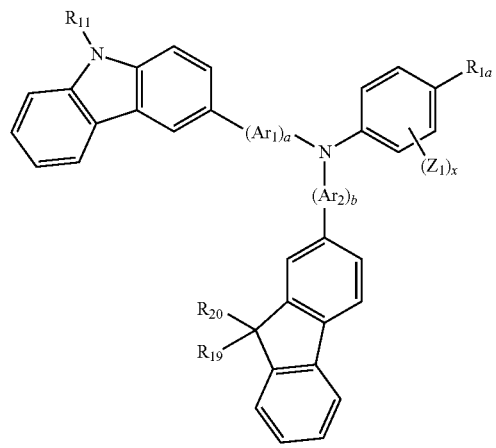

<Formula 2B>

<Formula 2C>
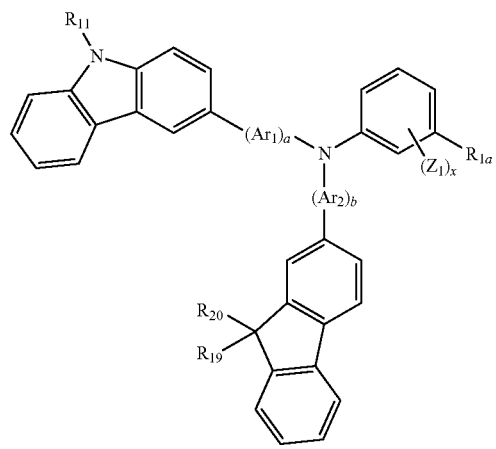
<Formula 2D>
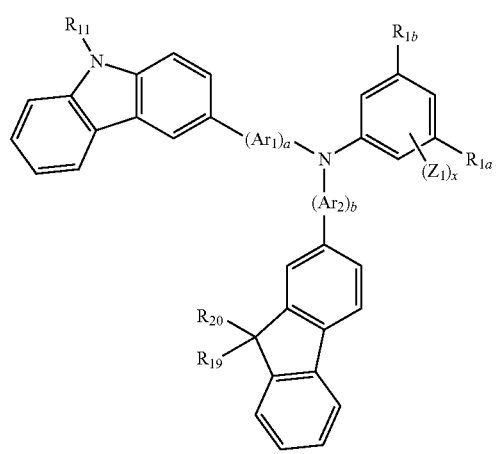
<Formula 2E>
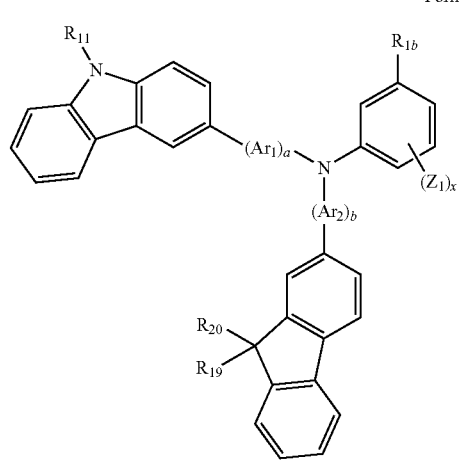
<Formula 2F>
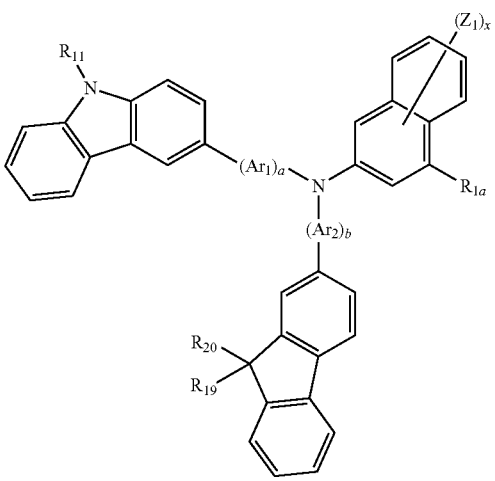
<Formula 2G>
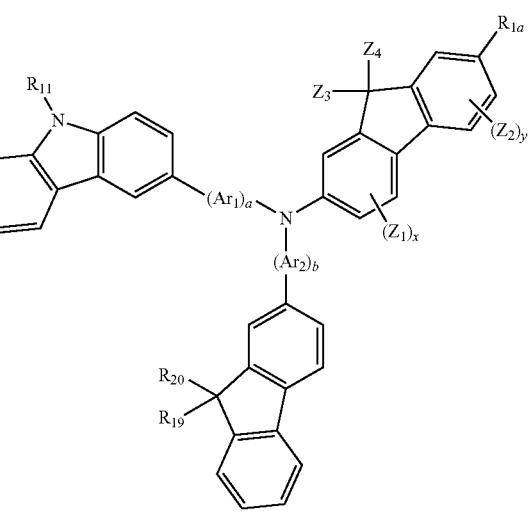
<Formula 2H>
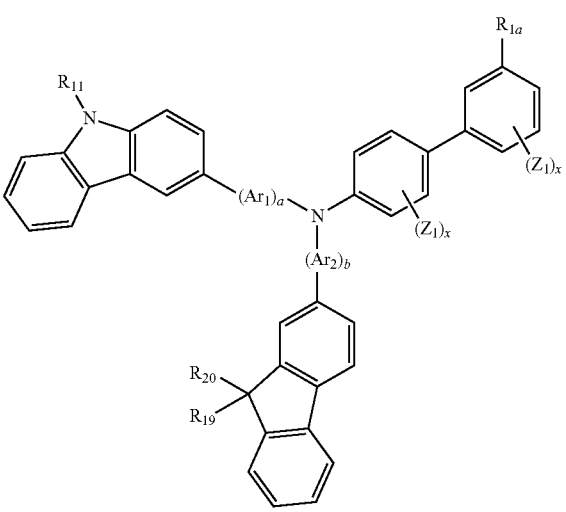

-continued

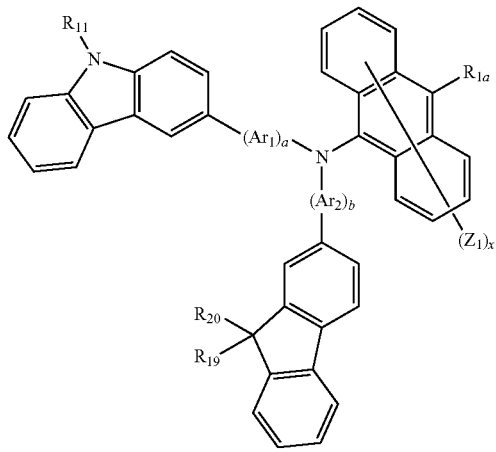

<Formula 2I>

<Formula 2J>

<Formula 2K> wherein in Formulae 2A to 2K,

Ar$_1$ and Ar$_2$ are each independently a substituted or unsubstituted C$_6$-C$_{60}$ arylene group;

a and b are each independently an integer of 0 to 5;

R$_{1a}$, R$_{1b}$, and R$_3$ are each independently a nitrogen atom-containing group;

R$_{11}$, R$_{19}$ and R$_{20}$ are each independently a substituted or unsubstituted C$_1$-C$_{60}$ alkyl group, or a substituted or unsubstituted C$_6$-C$_{60}$ aryl group;

Z$_1$ to Z$_4$ are each independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{60}$ cycloalkyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, —Si(Q$_1$)(Q$_2$)(Q$_3$), or —N(Q$_4$)(Q$_5$), and if x or y is 2 or more, a plurality of Z$_1$ or Z$_2$ are identical to or different from each other;

Q$_1$ to Q$_5$ are each independently a hydrogen atom, a deuterium atom, a halogen atom, a hydroxyl group, a cyano group, a nitro group, an amino group, an amidino group, hydrazine, hydrazone, a carboxylic group or salt thereof, a sulfonic acid group or salt thereof, a phosphoric acid group or salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{60}$ cycloalkyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, or a substituted or unsubstituted C$_2$-C$_{60}$ heteroaryl group;

X is an integer of 1 to 8; and y is an integer of 1 to 3.

7. The organic light-emitting diode of claim 1, wherein the second compound and the fourth compound are each independently at least one selected from Compounds 2, 8, 14, 15, 16, 20, 31, and 35 below:

COMPOUND 2

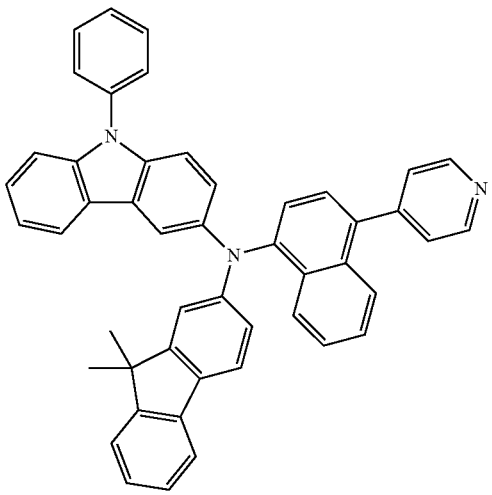

COMPOUND 8
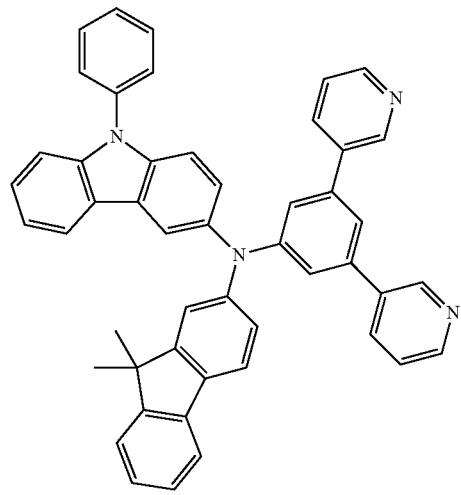
COMPOUND 15
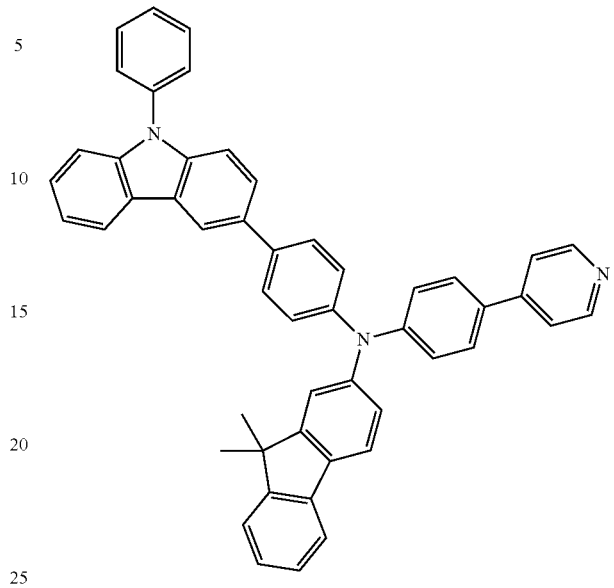
COMPOUND 14
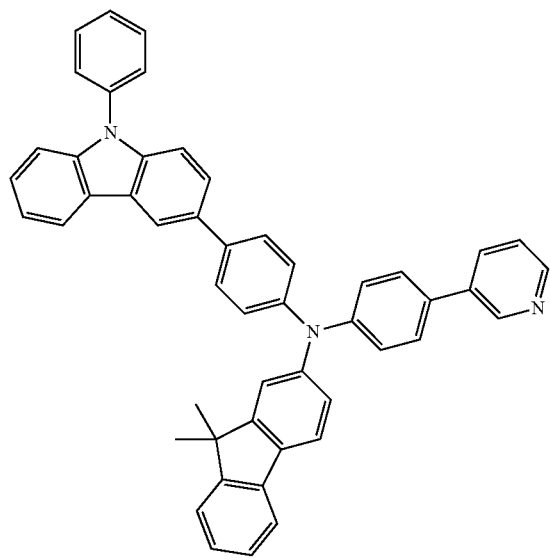
COMPOUND 16
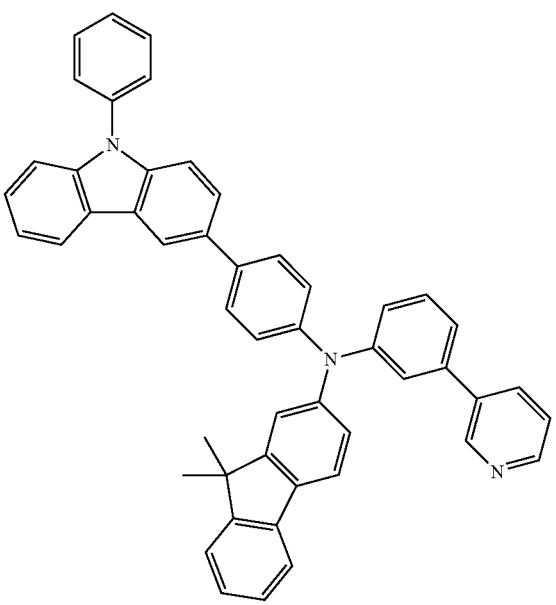

-continued

COMPOUND 20

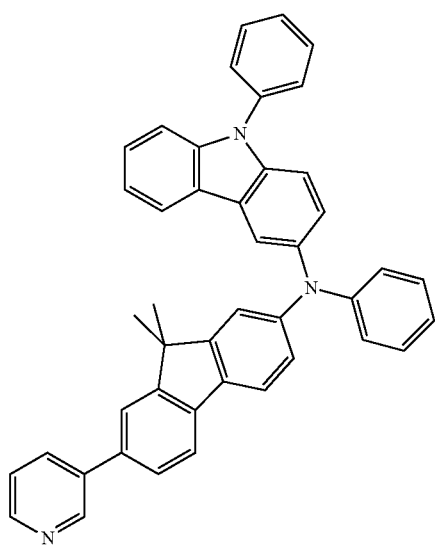

COMPOUND 31

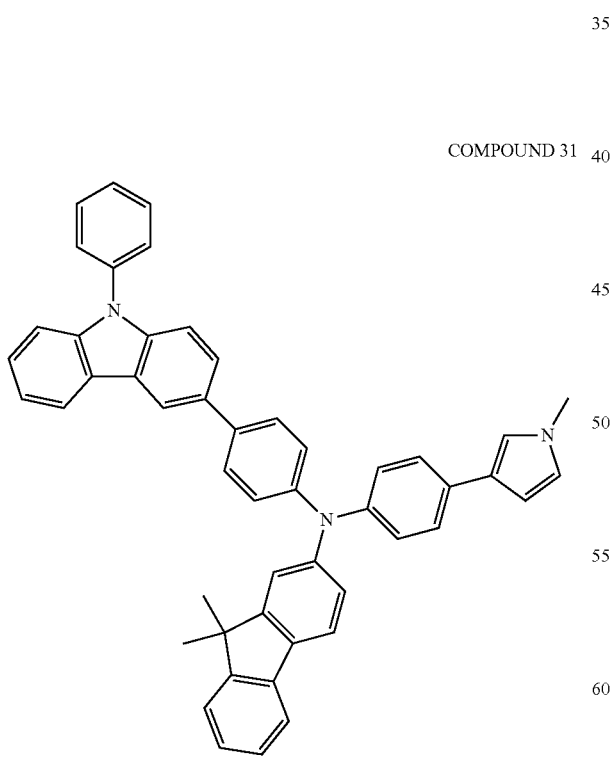

-continued

COMPOUND 35

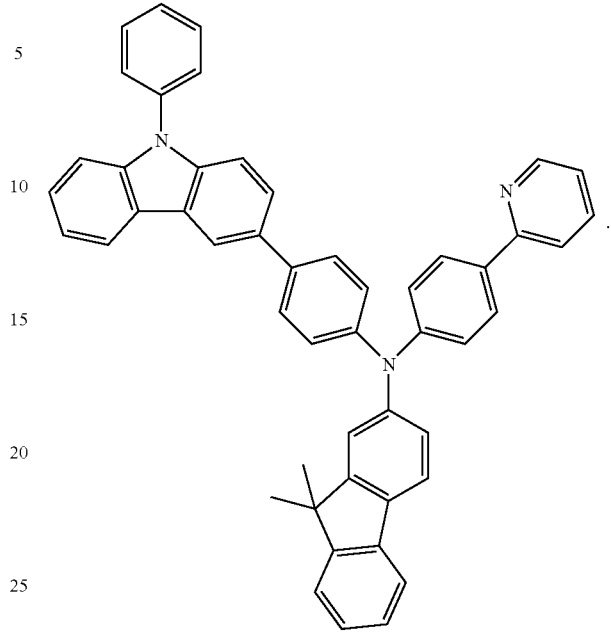

8. The organic light-emitting diode of claim 1, wherein the first charge generation material and the second charge generation material are each independently at least one selected from Compound 501 and 502 below:

<Compound 501>

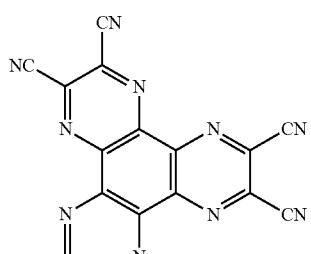

<Compound 502>

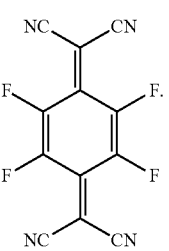

9. The organic light-emitting diode of claim 1, wherein a mixed weight ratio of the first compound and the second compound is in a range of 6:4 to 8:2.

10. The organic light-emitting diode of claim 1, wherein a mixed weight ratio of the third compound and the fourth compound is in a range of 6:4 to 8:2.

11. The organic light-emitting diode of claim 1, wherein a thickness of each of the first mixed layer and the second mixed layer is in a range of 40 nm to 60 nm.

12. The organic light-emitting diode of claim 1, wherein an amount of the first charge generation material is in a range of 1 to 3 parts by weight based on 100 parts by weight of the first charge generation layer.

13. The organic light-emitting diode of claim 1, wherein an amount of the second charge generation material is in a range of 1 to 3 parts by weight based on 100 parts by weight of the second charge generation layer.

14. The organic light-emitting diode of claim 1, wherein a thickness of each of the first charge generation layer and the second charge generation layer is in a range of 10 nm to 20 nm.

15. The organic light-emitting diode of claim 1, wherein the buffer layer comprises the compound represented by Formula 1.

16. The organic light-emitting diode of claim 1, wherein a thickness of the buffer layer is in a range of 0.1 nm to 30 nm.

17. The organic light-emitting diode of claim 1, wherein the first mixed layer contacts the first charge generation layer.

18. The organic light-emitting diode of claim 1, wherein the second mixed layer contacts the second charge generation layer.

19. The organic light-emitting diode of claim 1, wherein the organic light-emitting diode comprises at least one layer selected from a hole blocking layer, an electron transporting layer, an electron injection layer, and a functional layer having an electron transport function and an electron injection function, the at least one layer being between the emission layer and the second electrode.

20. A flat display device comprising: a transistor comprising a source, a drain, a gate, and an active layer; and the organic light-emitting diode of claim 1,
wherein the first electrode of the organic light-emitting diode is electrically connected to the source or the drain.

* * * * *